(12) United States Patent
He et al.

(10) Patent No.: US 8,704,155 B2
(45) Date of Patent: Apr. 22, 2014

(54) NANOSCALE OBJECT DETECTION USING A WHISPERING GALLERY MODE RESONATOR

(75) Inventors: Lina He, St. Louis, MO (US); Jiangang Zhu, St. Louis, MO (US); Sahin Kaya Ozdemir, St. Louis, MO (US); Lan Yang, St. Louis, MO (US); Da-Ren Chen, St. Louis, MO (US)

(73) Assignee: Washington University, St. Louis, MO (US)

( * ) Notice: Subject to any disclaimer, the term of this patent is extended or adjusted under 35 U.S.C. 154(b) by 564 days.

(21) Appl. No.: 12/966,785

(22) Filed: Dec. 13, 2010

(65) Prior Publication Data

US 2011/0139970 A1 Jun. 16, 2011

Related U.S. Application Data

(60) Provisional application No. 61/285,869, filed on Dec. 11, 2009.

(51) Int. Cl.
*G01J 9/00* (2006.01)

(52) U.S. Cl.
USPC .............. 250/227.18; 250/227.23; 356/319; 356/335; 977/881; 385/12

(58) Field of Classification Search
USPC .............. 250/216, 227.11, 227.14, 227.18, 250/227.23; 356/300, 301, 319, 320, 335, 356/336; 977/840, 880, 881; 385/12
See application file for complete search history.

(56) References Cited

U.S. PATENT DOCUMENTS

| | | | |
|---|---|---|---|
| 6,490,039 B2 * | 12/2002 | Maleki et al. ................ 356/436 |
| 6,580,532 B1 * | 6/2003 | Yao et al. ...................... 398/39 |
| 6,781,690 B2 * | 8/2004 | Armstrong et al. ........... 356/301 |
| 7,085,452 B1 * | 8/2006 | Lin et al. ......................... 385/39 |
| 7,228,016 B2 * | 6/2007 | Beausoleil ..................... 385/12 |
| 7,528,959 B2 | 5/2009 | Novotny et al. |
| 8,040,132 B2 * | 10/2011 | Klein et al. ................... 324/308 |
| 8,094,359 B1 * | 1/2012 | Matsko et al. ............... 359/239 |
| 2004/0263858 A1 | 12/2004 | Song et al. |
| 2005/0036151 A1 | 2/2005 | Gornick et al. |
| 2005/0073681 A1 | 4/2005 | Sevick-Muraca et al. |
| 2005/0128488 A1 | 6/2005 | Yelin et al. |
| 2005/0128566 A1 * | 6/2005 | Savchenkov et al. ........ 359/321 |
| 2005/0168753 A1 | 8/2005 | Butt et al. |

(Continued)

OTHER PUBLICATIONS

Colvin, Vicki L., "The potential environmental impact of engineered nanomaterials", Nature Biotechnology, Oct. 2003, pp. 1166-1170, vol. 21, No. 10, Nature Publishing Group.

(Continued)

*Primary Examiner* — John Lee
(74) *Attorney, Agent, or Firm* — Armstrong Teasdale LLP.

(57) ABSTRACT

Detection of individual objects using a light source and a whispering gallery mode (WGM) resonator. Light from the whispering gallery mode (WGM) resonator is analyzed. The presence of an object is determined based on mode splitting associated with the light received by the photodetector. For example, the presence of the object may be determined based on the distance between two whispering gallery modes and/or the linewidths of the two modes in a transmission spectrum. Alternatively, the presence of the object may be determined based on a beat frequency that is determined based on a heterodyne beat signal produced by combining split laser modes in the received light from a WGM microcavity laser.

20 Claims, 17 Drawing Sheets

(56) References Cited

U.S. PATENT DOCUMENTS

| | | | |
|---|---|---|---|
| 2006/0062508 A1* | 3/2006 | Guo et al. | 385/12 |
| 2006/0170931 A1* | 8/2006 | Guo et al. | 356/480 |
| 2007/0030492 A1 | 2/2007 | Novotny et al. | |
| 2007/0114477 A1 | 5/2007 | Teraoka et al. | |
| 2007/0206203 A1 | 9/2007 | Trainer | |
| 2008/0285606 A1* | 11/2008 | Kippenberg et al. | 372/32 |
| 2009/0136181 A1* | 5/2009 | Vollmer et al. | 385/50 |
| 2009/0191657 A1* | 7/2009 | Yang et al. | 438/31 |
| 2009/0256136 A1* | 10/2009 | Tan et al. | 257/22 |
| 2009/0310140 A1* | 12/2009 | Smith et al. | 356/480 |
| 2009/0310902 A1* | 12/2009 | Smith et al. | 385/12 |
| 2010/0026300 A1* | 2/2010 | Klein et al. | 324/316 |
| 2010/0326200 A1* | 12/2010 | Sheverev et al. | 73/800 |
| 2011/0019186 A1* | 1/2011 | Himmelhaus et al. | 356/317 |
| 2011/0139970 A1* | 6/2011 | He et al. | 250/227.18 |
| 2011/0253897 A1* | 10/2011 | Saeedkia et al. | 250/358.1 |
| 2011/0253909 A1* | 10/2011 | Himmelhaus et al. | 250/492.1 |
| 2011/0277540 A1* | 11/2011 | Ioppolo et al. | 73/31.03 |
| 2012/0194893 A1* | 8/2012 | Maleki et al. | 359/246 |
| 2012/0268731 A1* | 10/2012 | Zhu et al. | 356/73 |

OTHER PUBLICATIONS

Hoet, Peter HM, et al., "Nanoparticles—known and unknown health risks", Journal of Nanobiotechnology, Dec. 8, 2004, 15 pages, DOI:10.1186/1477-3155-2-12, BioMed Central.

Nie, Shuming, et al., "Probing Single Molecules and Single Nanoparticles by Surface-Enhanced Raman Scattering", Science, Feb. 21, 1997, pp. 1102-1106, DOI: 10.1126/science.275.5303.1102, American Association for the Advancement of Science.

Patolsky, Fernando, et al., "Electrical detection of single viruses", PNAS, Sep. 28, 2004, pp. 14017-14022, vol. 101, No. 39, The National Academy of Sciences of the USA.

Naik, A.K., et al., "Towards single-molecule nanomechanical mass spectrometry", Nature Nanotechnology, Jun. 21, 2009, pp. 445-450, DOI: 10.1038/NNano.2009.152, Macmillan Publishers Limited.

Burg, Thomas P., et al., "Weighing of biomolecules, single cells and single nanoparticles in fluid", Nature, Apr. 26, 2007, pp. 1066-1069, vol. 446, DOI: 10.1038/nature05741, Nature Publishing Group.

Wang, Shaopeng, et al., Label-free imaging, detection, and mass measurement of single viruses by surface plasmon resonance, 5 pages, DOI: 10.1073/pnas.1005264107, PNAS, (2010).

Mitra, Anirban, et al., "Nano-optofluidic Detection of Single Viruses and Nanoparticles", ACS NANO, 2010, pp. 1305-1312, vol. 4, No. 3, American Chemical Society.

Vahala, Kerry J., "Optical microcavities", Nature, Aug. 14, 2003, pp. 839-846, vol. 424, Nature Publishing Group.

Armani, D.K., et al., "Ultra-high-Q toroid microcavity on a chip", Nature, Feb. 27, 2003, pp. 925-928, vol. 421, Nature Publishing Group.

Vollmer, Frank, et al., "Whispering-gallery-mode biosensing: label-free detection down to single molecules", Nature Methods, Jun. 27, 2008, pp. 591-596, vol. 5, No. 7, DOI:10.1038/NMETH.1221, Nature Publishing Group.

Shopova, S.I., et al., "Ultrasensitive nanoparticle detection using a portable whispering gallery mode biosensor driven by a periodically poled lithium-niobate frequency doubled distributed feedback laser", Review of Scientific Instruments, Oct. 27, 2010, pp. 103110-1-103110-4, vol. 81, American Institute of Physics.

Yalcin, Ayca, et al., "Optical Sensing of Biomolecules Using Microring Resonators", IEEE Journal of Selected Topics in Quantum Electronics, Jan. 2006, pp. 148-155, vol. 12, No. 1.

White, Ian M., et al., "Liquid-core optical ring-resonator sensors", Optics Letters, Feb. 9, 2006, pp. 1319-1321, vol. 31, No. 9, Optical Society of America.

Zhu, Jiangang, et al., "On-chip single nanoparticle detection and sizing by mode splitting in an ultrahigh-Q microresonator", Nature Photonics, Dec. 13, 2009, pp. 46-49, DOI: 10.1038/NPHOTON.2009.237, Macmillan Publishers Limited.

Weiss, D.S., et al., "Splitting of high-Q Mie modes induced by light backscattering in silica microspheres", Optics Letters, Sep. 15, 1995, pp. 1835-1837, vol. 20, No. 18, Optical Society of America.

Gorodetsky, Michael L., et al., "Rayleigh scattering in high-Q microspheres", Journal of the Optical Society of America, Jun. 2000, pp. 1051-1057, vol. 17, No. 6, Optical Society of America.

Mazzei, A., et al., "Controlled Coupling of Counterpropagating Whispering-Gallery Modes by a Single Rayleigh Scatterer: A Classical Problem in a Quantum Optical Light", Physical Review Letters, Oct. 26, 2007, pp. 173603-1 to 173603-4, PRL 99, 173603, The American Physical Society.

Chantada, L., et al., "Optical resonances in microcylinders: response to perturbations for biosensing", Journal of the Optical Society of America, Aug. 2008, pp. 1312-1321, vol. 25, No. 8, Optical Society of America.

Neelen, R. Centeno, et al., "Frequency splitting of the longitudinal modes of a ring dye laser due to backscattering", Journal of the Optical Society of America, May 1991, pp. 959-969, vol. 8, No. 5, Optical Society of America.

Yang, Lan, et al., A 4-Hz Fundamental Linewidth on-chip Microlaser, 2007, 2 pages, OSA 1-55752-834-9, Optical Society of America.

He, Lina, et al., "Ultrasensitive detection of mode splitting in active optical microcavities", Physical Review, Nov. 11, 2010, pp. 053810-1 to 053810-4, vol. A 82, DOI: 10.1103/PhysRevA.82.053810, The American Physical Society.

Yang, Lan, et al., "Erbium-doped and Raman microlasers on a silicon chip fabricated by the sol-gel process", Applied Physics Letters, Feb. 25, 2005, pp. 091114-1 to 091114-3, vol. 86, 091114, DOI: 10.106311.1873043, American Institute of Physics.

Zhu, Jiangang, et al., "Controlled manipulation of mode splitting in an optical microcavity by two Rayleigh scatterers", Optics Express, Oct. 26, 2010, pp. 23535-23543,vol. 18, No. 23, Optical Society of America.

He, Lina, et al., "Scatterer induced mode splitting in poly(dimethylsiloxane) coated microresonators", Applied Physics Letters, Jun. 1, 2010, pp. 221101-1 to 221101-3, vol. 96, 221101, DOI: 10.1063/1.3435480, American Institute of Physics.

Kim, Woosung, et al., "Demonstration of mode splitting in an optical microcavity in aqueous environment", Applied Physics Letters, Aug. 18, 2010, pp. 071111-1 to 071111-3, vol. 97, 071111, DOI: 10.1063/1.3481352, American Institute of Physics.

* cited by examiner

NANOSCALE OBJECT DETECTION USING A WHISPERING GALLERY MODE RESONATOR

CROSS REFERENCE TO RELATED APPLICATIONS

This application claims the benefit of U.S. Provisional Patent Application No. 61/285,869, filed 11 Dec. 2009, which is hereby incorporated by reference in its entirety.

STATEMENT REGARDING FEDERALLY SPONSORED RESEARCH & DEVELOPMENT

This invention was made with government support under NSF-DMR-0907467 awarded by The National Science Foundation. The government has certain rights in the invention.

BACKGROUND

With recent progress in nanotechnology, nanoparticles of different materials and sizes have been synthesized and engineered as key components in various applications ranging from solar cell technology to the detection of biomolecules. Meanwhile, nanoparticles generated by vehicles and industry have become recognized as potential threats to health and environment. Microscopy and spectroscopy techniques have played central roles in single nanoparticle/molecule detection. However, their widespread use has been limited by bulky and expensive instrumentation, long processing time, and/or the need for labeling. Light scattering techniques, while suitable for label-free detection, are hindered by the extremely small scattering cross-sections of single nanoparticles.

SUMMARY

The presence of an object, such as a nanoparticle and/or a virion, is detected using a whispering gallery mode (WGM) resonator. An optical fiber is positioned adjacent the WGM resonator, such that light passing through the optical fiber is coupled into the WGM resonator, where it propagates in two opposite directions. The propagation of the light is affected by the presence of objects proximate to (e.g., adsorbed on) the WGM resonator. The light is decoupled from the WGM resonator to the optical fiber, which carries the light to a device that includes photodetector. At the device, the presence of an object is determined based on mode splitting associated with the light received by the photodetector. For example, a transmission spectrum may be created based on the received light, and the distance between two modes and/or the linewidths of the two modes may be used to determine the presence of an object and measure its polarizability. In another example, two modes in the received light are combined to create a heterodyne beat signal, and a beat frequency is determined based on the heterodyne beat signal. The presence of an object is determined based on the beat frequency.

BRIEF DESCRIPTION OF THE DRAWINGS

The embodiments described herein may be better understood by referring to the following description in conjunction with the accompanying drawings.

DETAILED DESCRIPTION

Figure 1:
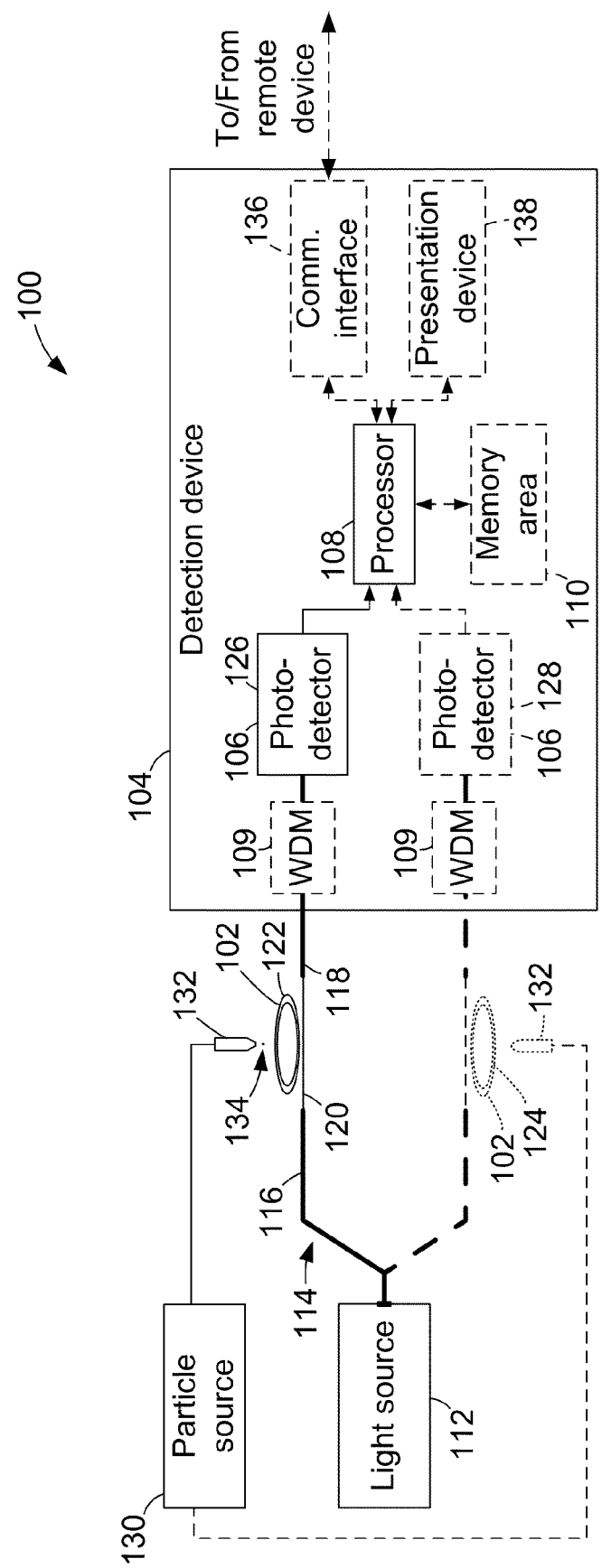
FIG. 1 is a diagram illustrating an example system for detecting an object.

Embodiments described herein facilitate detecting the presence and the polarizability, which is related to the size, the composition, and/or the refractive index, of one or more objects on the surface of a whispering gallery mode (WGM) resonator. Accordingly, such embodiments enable the creation of a portable, inexpensive, and high-resolution device capable of real-time and in-situ detection of particles surpassing current detection limits.

In exemplary embodiments, the presence of an object, such as a nanoscale object, is determined based on light received from WGM resonator. As used herein, the term "nanoscale object" refers to any synthetic or natural subwavelength (e.g., smaller than the wavelength of the light used to detect) object that scatters light. Nanoscale objects may also be referred to as nanoparticles and may include, for example metallic particles, non-metallic particles, plasmonic particles, non-plasmonic particles, viruses (e.g., virions), bacteria, and/or biomolecules.

A WGM resonator offers a highly confined microscale mode volume and an ultra-high quality factor ("Q"), enabling strong light-matter interactions that can be used for ultra-sensitive optical detection. Such detection may be enabled, at least in part, by the existence of two standing wave modes produced by the presence of an object on the WGM resonator and/or within an evanescent field of the WGM resonator. More specifically, object binding splits a WGM into two spectrally shifted resonance modes. The split modes share a single resonator and are therefore subject to the same noise, allowing for a self-referencing detection system relatively immune to noise.

Such embodiments facilitate compact and/or portable in-situ detection and sizing systems with single-object resolution which do not require labeling of objects or predetermined information regarding the presence of objects in the medium tested. For example, an entire detection system may be integrated into a single chip or die, facilitating cost-efficient manufacture and packaging. Furthermore, this technique enables extracting accurate object size information with a single-shot measurement in a micro-scale device.

Some embodiments are described herein in with reference to particular objects, such as virions. However, the methods described are generally applicable to nanoscale objects, regardless of material and/or internal structure. It is contemplated that the embodiments provided may be practiced with single or multiple nanoscale objects (e.g., nanoparticles, atoms, and/or virions).

In exemplary embodiments, a silica microtoroidal resonator includes two degenerate WGMs with the same resonant frequency and evanescent field distributions but opposite propagation directions. The two WGMs may be referred to as a clockwise mode and a counter-clockwise mode. Other types of WGM resonators that support such degenerate modes, such as a sphere, a disk, or a cylinder, may be used in addition to or in place of a microtoroidal resonator. It is contemplated that a resonator with a substantially circular structure may be used. In one embodiment, the resonator is approximately 10 micrometers (also known as microns, μm) to 1000 μm in size. Resonators of other dimensions are also contemplated.

A perturbation in the mode volume, such as surface roughness, material inhomogeneity, or a scatterer, causes the resonator to deviate from perfect azimuthal symmetry, lifting the degeneracy of the WGM modes to split the resonance into a doublet. When light received from a WGM resonator is represented in a transmission spectrum, such "mode splitting" appears as a distance (in hertz or megahertz, for example) between the two modes of the doublet. Mode splitting may be used to determine that an object is present and/or to determine one or more properties of the object. In some embodiments, object presence and/or at least one object property is determined based on the distance between the standing wave modes and the linewidths of the standing wave modes.

FIG. 1 is a diagram illustrating a system 100 for detecting an object. System 100 includes a whispering gallery mode (WGM) resonator 102 and a detection device 104. Detection device 104 includes a photodetector 106 configured to receive light emitted by or coupled out of WGM resonator 102. Detection device 104 also includes a processor 108 that is coupled to photodetector 106. Processor 108 is capable of executing instructions and may include one or more processing units (e.g., in a multi-core configuration).

In some embodiments, WGM resonator 102 is "passive" (e.g., not populated with a gain medium). In such embodiments, processor 108 is programmed to create a transmission spectrum based on light received from WGM resonator 102 and to determine the presence of an object based on the transmission spectrum, as described in more detail below with reference to FIGS. 4-11.

In some embodiments, WGM resonator 102 includes a gain medium and may be referred to as "active." In such embodiments, photodetector 106 is configured to combine split laser modes that are included in the light received from WGM resonator 102, optionally filtered by a wavelength-division multiplexer (WDM) 109, to create a heterodyne beat signal. Processor 108 is programmed to determine a beat frequency based on the heterodyne beat signal and to detect the presence of an object based on the beat frequency, as described in more detail below with reference to FIGS. 12-21.

In some embodiments, detection device 104 includes a memory area 110 coupled to processor 108. Memory area 110 is any device allowing information, such as executable instructions and/or other data, to be stored and retrieved. Memory area 110 may include one or more computer readable media.

Memory area 110 may be configured to store data, including encoded instructions that are executable by processor 108 to perform one or more of the operations described herein. Memory area 110 may also be configured to store object detection data, such as, but not limited to, transmission spectra, heterodyne beat signals, beat frequencies, object detection events, and/or object properties.

In one embodiment, memory area 110 is configured to store transmission spectra, and processor 108 is programmed to compare a current transmission spectrum to a previously stored transmission spectrum from memory area 110. For example, processor 108 may be programmed to subtract the previously recorded transmission spectrum from the current transmission spectrum to create a difference and to determine a presence and/or a property of one or more objects based on the difference. For example, the appearance of a second mode where only one mode was previously present may indicate the presence of an object. Similarly, a change in the distance between the first mode and the second mode may indicate the presence of an additional object. Memory area 110 may be configured to store the current transmission spectrum, which may be subsequently used by processor 108 as a previously stored transmission spectrum.

System 100 may also include a light source 112 and an optical fiber 114. In one embodiment, such as with a passive resonator, light source 112 is a laser, which may be optimized so that no thermal effect is present in the transmission spectrum created by processor 108. Light source 112 may be tunable, such that light may be produced over a range of frequency.

Optical fiber 114 includes a first normal portion 116, a second normal portion 118, and a tapered portion 120 between first normal portion 116 and second normal portion 118. Tapered portion 120 has a diameter smaller than the wavelength of light transmitted by light source 112. An evanescent field surrounds at least a part of tapered portion 120. With WGM resonator 102 positioned proximate to tapered portion 120 (e.g., within the evanescent field), at least some light carried by optical fiber 114 is transmitted to or coupled into WGM resonator 102. Similarly, light is coupled out of or decoupled from WGM resonator 102 and coupled into tapered portion 120.

In exemplary embodiments, WGM resonator 102 is configured to receive light from tapered portion 120 and to allow the light to propagate within WGM resonator 102. For example, a photon may travel around an ultra-high-Q WGM resonator 102 over one million times. The repeated circulation of light in WGM resonator 102 may amplify the effect of standing wave modes, facilitating more accurate detection of objects, as described herein. Similarly, light is coupled out of, or decoupled from, WGM resonator 102. Light is coupled out of WGM resonator 102. Light may be emitted by WGM resonator 102 proximate to tapered portion 120 of optical fiber 114 and transmitted by second normal portion 118 to detection device 104.

System 100 may include a plurality of WGM resonators 102. As illustrated in FIG. 1, system 100 includes a first WGM resonator 122 and a second WGM resonator 124. Optical fiber 114 is split, such that light source 112 provides light to both first WGM resonator 122 and second WGM resonator 124. In an alternative embodiment, a light source 112 is provided for each WGM resonator 102.

Detection device 104 includes one photodetector 106 for each WGM resonator 102. As illustrated, detection device 104 includes a first photodetector 126 configured to receive light from first WGM resonator 122 and a second photodetector 128 configured to receive light from second WGM resonator 124. Both first photodetector 126 and second photodetector 128 are coupled to processor 108. Processor 108 may be programmed to create a transmission spectrum for each photodetector 106 and to determine a presence, a size, a refractive index, and/or a position of one or more objects based on each created transmission spectrum, as described above.

In some embodiments, system 100 includes one or more particle sources 130. Particle source 130 is configured to acquire one or more nanoparticles and direct the nanoparticles to a nozzle 132. Particle source 130 may be configured to filter or select particles based on one or more particle properties, including size, electrical mobility, shape, composition, and/or any other property of interest. In one embodiment, particle source 130 includes a differential mobility analyzer (DMA). Particle source may include one or more collections of nanoparticles (e.g., having known properties) and/or may draw samples from a medium to be tested, such as, but not limited to, ambient air, a fluid in a surrounding environment, and/or a fluid in a container. In addition, or alternatively, WGM resonator 102 may be directly exposed to the medium to be tested. In some embodiments, particle source 130 and nozzle 132 are omitted.

Nozzle 132 is positioned proximate to WGM resonator 102. For example, nozzle 132 may be separated from WGM resonator 102 by approximately 150 µm. In one embodiment, nozzle 132 has a tip inner diameter of approximately 80 µm.

In one embodiment, nozzle 132 is configured to direct an object 134 received from particle source 130 toward WGM resonator 102, such that object 134 is adsorbed on WGM resonator 102. If multiple WGM resonators 102 are provided, system 100 may include a nozzle 132 for each WGM resonator 102. Multiple nozzles 132 may be configured to receive nanoparticles from a single particle source 130. Alternatively, system 100 may include multiple particle sources 130, each of which is coupled to one or more nozzles 132.

Detection device 104 may include an output device, such as a communication interface 136 and/or a presentation device 138. Communication interface 136 may include, for example, at least one electrical conductor, serial data communication device, parallel data communication device and/or network adapter, whether wired or wireless. In one embodiment, communication interface 136 is configured to transmit a detection signal indicating the presence, the size, and/or the refractive index of one or more detected objects. The transmitted detection signal may be received by one or more remote devices, such as an operating console, a monitoring device, and/or any other computing device.

Presentation device 138 may include, but is not limited to, a display device and/or an audio output device. In one embodiment, presentation device 138 is configured to indicate the presence, the size, and/or the refractive index of one or more detected objects. For example, presentation device 138 may emit an audible noise when an object is detected and/or may display information about detected objects.

In some embodiments, multiple components of system 100 are integrated into a single hardware package. For example, light source 112, optical fiber 114, one or more WGM resonators 102, and detection device 104 may be included on a single die or silicon chip.

In one embodiment, system 100 is implemented as a fly-by particle counting and sizing system. In such a configuration, nozzle 132 is configured to direct object 134 through an evanescent field of WGM resonator 102, rather than directly at the surface of WGM resonator 102. As object 134 passes through the evanescent field of WGM resonator 102, the presence of object 134 results in mode splitting, which is detected and/or analyzed to detect the presence and/or a property of object 134, as described herein. When the particle departs the evanescent field, the transmission spectrum reverts to its previous state.

Figure 2:
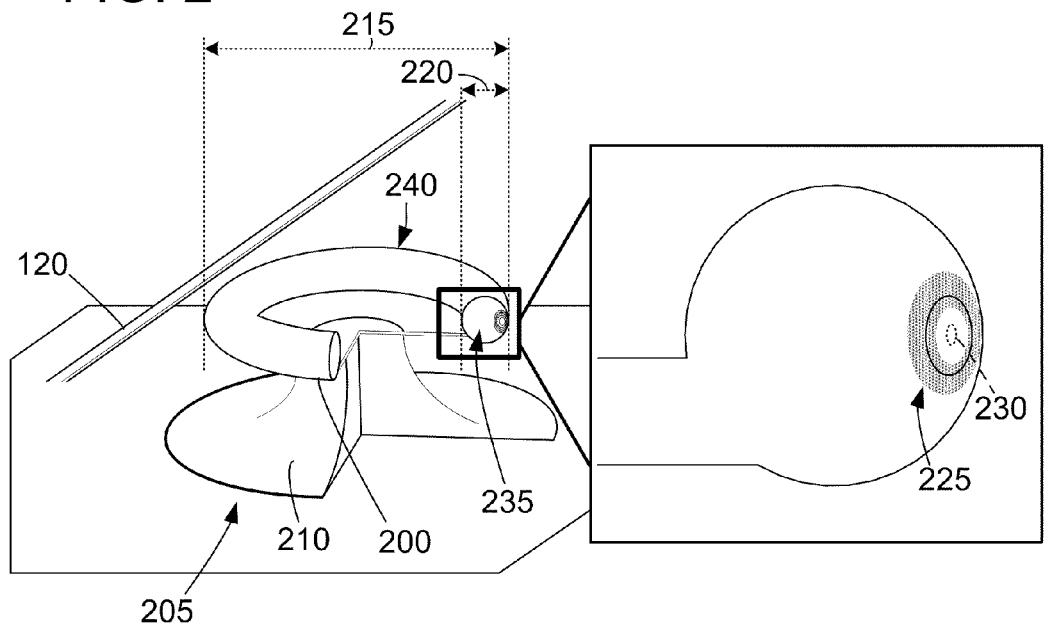
FIG. 2 is a diagram illustrating an example microtoroidal whispering gallery mode (WGM) resonator for use with the system shown in FIG. 1.

FIG. 2 is a diagram illustrating an example microtoroidal WGM resonator 200 for use with system 100. Microtoroidal WGM resonator 200 is fabricated on or mounted to a surface 205 by a base 210. In exemplary embodiments, surface 205 and base 210 are constructed of silicon, and microtoroidal WGM resonator 200 is constructed of silica. Microtoroidal WGM resonator 200 may be fabricated from a silica layer (e.g., approximately 2 millimeters in thickness) on a silicon wafer. For example, microtoroidal WGM resonator 200 may be formed from the silica layer by laser reflow, xenon difluoride ($XeF_2$) etching, photolithography followed by hydrofluoric acid (HF) etching, and/or any suitable fabrication means. Such an embodiment facilitates integrating one or more WGM resonators 102 with other components of system 100 on a single silicon wafer. In some embodiments, microtoroidal WGM resonator 200 is doped with a gain medium and is referred to as an active resonator. In other embodiments, no gain medium is included, and microtoroidal WGM resonator 200 is referred to as a passive resonator.

In some embodiments, microtoroidal WGM resonator 200 has a major diameter 215 of approximately 30 µm to 200 µm. In one exemplary embodiment, microtoroidal WGM resonator 200 has a minor diameter 220 of approximately 5 µm to 30 µm and has a mode volume of approximately 200 µm$^3$. Microtoroidal WGM resonator 200 is positioned proximate to tapered portion 120 of optical fiber 114.

Figure 3:
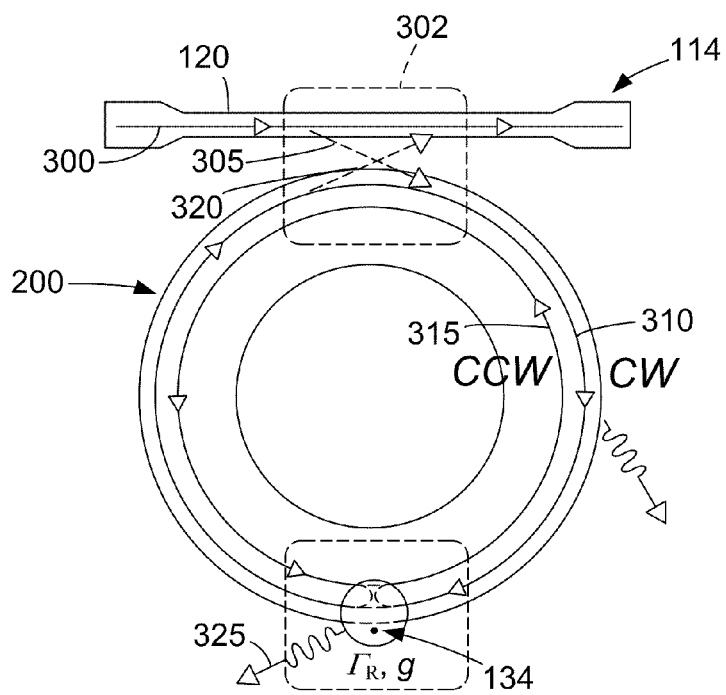
FIG. 3 is a diagram illustrating light propagation in the optical fiber and the microtoroidal WGM resonator shown in FIG. 2.

Microtoroidal WGM resonator 200 includes two degenerate WGMs with the same resonant frequency and the same evanescent field distribution but opposite propagation directions, as shown in FIG. 3. FIG. 2 illustrates a distribution of a Wgm evanescent field 225 on the periphery of microtoroidal WGM resonator 200. Nozzle 132 (shown in FIG. 1) may be configured to direct object 134 toward Wgm evanescent field 225. For example, nozzle 132 may be configured to deposit object 134 in the evanescent field of Wgm evanescent field 225 near a center 230 of Wgm evanescent field 225 and/or the mode, where the object may have a pronounced effect on the transmission spectrum, as described in more detail below. In addition, surface 205 may be configured to exert an electrical field on object 134 to attract object 134 toward microtoroidal WGM resonator 200.

Microtoroidal WGM resonator 200 includes a cavity 235, which may be doped with a gain medium in an "active" application, such that an input light of shorter wavelength with power above a lasing threshold generates a laser light of longer wavelength. The structure of microtoroidal WGM resonator 200 surrounds cavity 235, defining an outer surface 240. In some embodiments, outer surface 240 includes (e.g., is coated with) a selective coating. The selective coating may be selected to bind one or more particular types of objects (e.g., specific compounds and/or virions) to outer surface 240, while other types of objects may not easily bind to the object adhesive. Such embodiments facilitate detecting the presence of one or more objects of interest.

FIG. 3 is a diagram illustrating light propagation in optical fiber 114 and microtoroidal WGM resonator 200. Proximate to tapered portion 120, light 300 transmitted by optical fiber 114 produces an evanescent field 302 about tapered portion 120. Microtoroidal WGM resonator 200 is positioned within the evanescent field of tapered portion 120 and receives at least some light 305 from optical fiber 114. Viewed from above, within microtoroidal WGM resonator 200, a clockwise WGM 310 is associated with light propagating in a clockwise direction, and a counter-clockwise WGM 315 is associated with light propagating in a counter-clockwise direction.

Light is confined within microtoroidal WGM resonator 200. For example, light may circulate through microtoroidal WGM resonator 200 up to approximately one million times before being completely dissipated. Light coupled out of microtoroidal WGM resonator 200 is received by tapered portion 120 and carried toward detection device 104.

As a result of repeated interactions between the confined light and object 134, which is deposited on the surface of microtoroidal WGM resonator 200, the effect of object 134 on light 320 is amplified, producing very high quality output.

Embodiments provided herein are operable with passive and/or active WGM resonators 200, as described in more detail below.

Passive WGM Resonator

Referring to FIG. 1, in some embodiments, WGM resonator 102 is a passive WGM resonator that includes no gain medium, and light source 112 is a tunable laser. In such embodiments, processor 108 is programmed to create a transmission spectrum based on the light received from WGM resonator 102. The transmission spectrum indicates transmission of light by WGM resonator 102 over a frequency range. Processor 108 may be programmed to create the transmission spectrum based on input received from photodetector 106 over a sampling period. In exemplary embodiments, the sampling period is approximately 1 millisecond or less. If the light coupled out of WGM resonator 102 originates at a tunable laser, the sampling period may be defined based on a wavelength scanning speed of the tunable laser. For example, the sampling period may be substantially equal to the amount of time required for the tunable laser to scan a frequency range of interest (e.g., spanning about 500 to 1000 megahertz).

Processor 108 is also programmed to identify within the transmission spectrum a first mode and a second mode, each of which represents a portion of the transmission spectrum associated with decreased transmission. Processor 108 is further programmed to determine a presence, a size, a composition, a refractive index, and/or a position of an object based on the first mode and the second mode. For example, processor 108 may be programmed to determine the presence of an object and/or to measure the polarizability of an object based on the distance between the first mode and the second mode, the linewidth of the first mode, and/or the linewidth of the second mode.

Processor 108 may also be programmed to determine a presence of one or more additional objects based on the first mode and the second mode. For example, processor 108 may be programmed to determine, based on the distance between the first mode and the second mode, the linewidth of the first mode, and/or the linewidth of the second mode, that more than one object is adsorbed on and/or proximate to WGM resonator 102.

Figure 4:
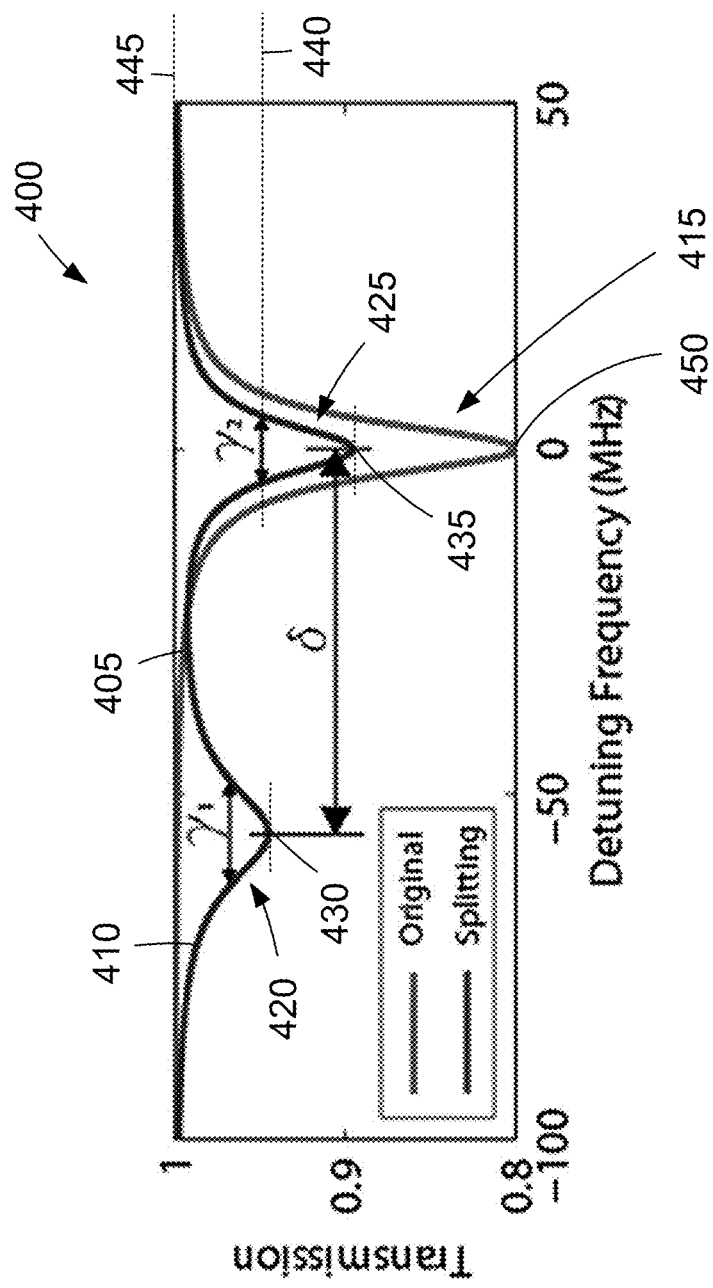
FIG. 4 is a chart illustrating an example zero-particle transmission spectrum and an example one-particle transmission spectrum based on light coupled out of a passive WGM resonator.

FIG. 4 is a chart 400 illustrating an example zero-particle transmission spectrum 405 and an example one-particle transmission spectrum 410 based on light coupled out of WGM resonator 102. For comparison, zero-particle transmission spectrum 405, produced in the absence of a nanoparticle, is overlaid on one-particle transmission spectrum 410, produced in the presence of one nanoparticle.

Zero-particle transmission spectrum 405 indicates a single Lorentzian resonance or a single mode 415. After a particle is deposited on WGM resonator 102, standing wave modes (SWMs) are formed, as indicated by double Lorentzian resonances, depicted as a first mode 420 and a second mode 425 in one-particle transmission spectrum 410. Successive depositions of particles may introduce variation in first mode 420 and second mode 425, as described below with regard to FIG. 6.

Referring again to FIGS. 2-4, the WGMs within WGM resonator 102 are associated with a distribution of evanescent fields 225, and a nanoparticle in evanescent field 225 acts as a scatterer. A portion 325 of the scattered light is lost to the environment, creating an additional damping channel, while the remaining light couples back into the resonator and induces coupling between clockwise WGM 310 and counter-clockwise WGM 315. The degeneracy of clockwise WGM 310 and counter-clockwise WGM 315 is consequently lifted, creating SWMs that are split in frequency, as represented by first mode 420 and second mode 425 of one-particle transmission spectrum 410. In some embodiments, in the absence of object 134, clockwise WGM 310 and counter-clockwise WGM 315 share a single set of evanescent fields 225.

Figure 5:
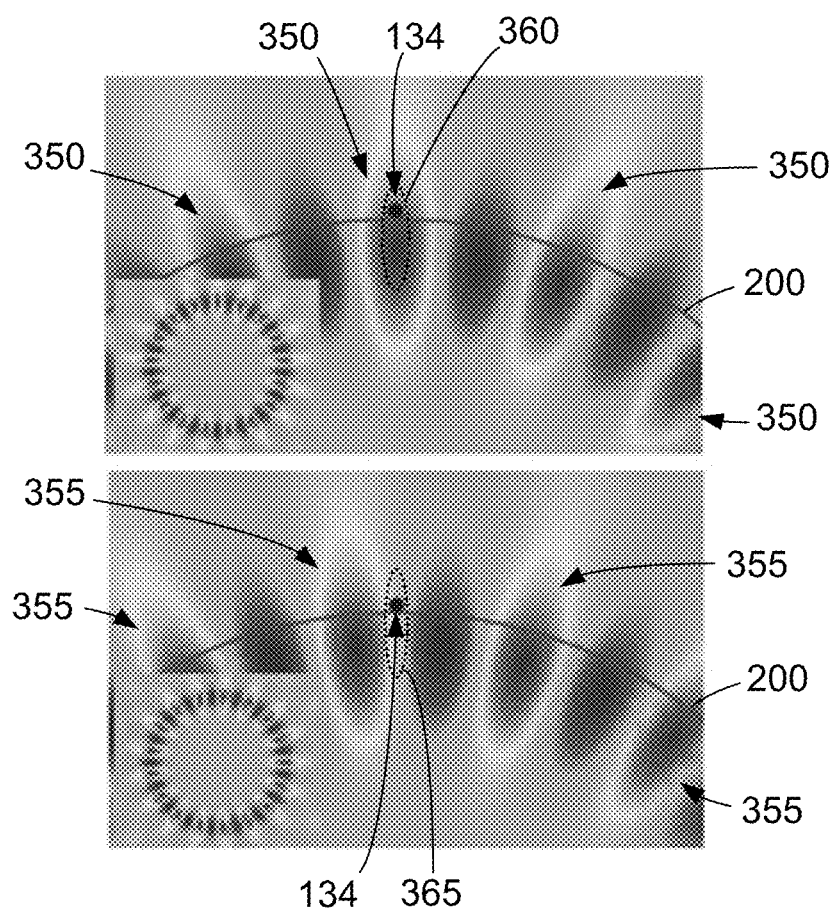
FIG. 5 is an example illustration of WGM evanescent fields relative to the position of a nanoparticle deposited on the microtoroidal WGM resonator shown in FIG. 2.

FIG. 5 is an example illustration of WGM evanescent fields relative to the position of object 134 deposited on microtoroidal WGM resonator 200. In the presence of object 134, clockwise WGM 310 and counter-clockwise WGM 315 are redistributed according to the position of object 134, creating a symmetric mode (SM) with SM evanescent fields 350 and an asymmetric mode (ASM) with ASM evanescent fields 355.

Referring again to FIGS. 4 and 5, the symmetric mode (SM) locates object 134 at an anti-node 360, and the asymmetric mode (ASM) locates object 134 at a node 365. Consequently, the SM experiences frequency shift and linewidth broadening, as indicated by first mode 420 of one-particle transmission spectrum 410. First mode 420 corresponds to the SM, and second mode 425 corresponds to the ASM.

In one embodiment, a frequency shift is determined by calculating a distance (δ) between first mode 420 and second mode 425. Specifically, the distance δ is determined between a nadir 430 of first mode 420 and a nadir 435 of second mode 425. The linewidth (γ) of a mode may be calculated by determining the width of the mode at a half-amplitude level. For example, a linewidth (γ$_2$) of second mode 425 is determined at a vertical position 440, which is equidistant from nadir 435 and a baseline 445. A linewidth (γ$_1$) is similarly determined for first mode 420. In one embodiment, a single nanoparticle is detectable if δ>(γ$_1$+γ$_2$)/2.

A coupling strength g is quantified by the doublet splitting g=πδ, where δ is the distance between first mode 420 and second mode 425, as described above. The additional linewidth broadening may be expressed as Γ$_R$=π|γ$_1$−γ$_2$|.

In some embodiments, the resonance wavelength prior to splitting, denoted as λ, is equal to the absolute wavelength at a nadir 450 of zero-particle transmission spectrum 405 or at nadir 435 of one-particle transmission spectrum 410. The size of object 134 is expressed as a radius length R. If radius R<<λ, particle-WGM interaction may induce a dipole represented by particle polarizability α, as expressed by Equation 1 below.

$$\alpha = 4\pi R^3 \frac{(\varepsilon_p - \varepsilon_m)}{(\varepsilon_p + 2\varepsilon_m)} \quad (1)$$

In Equation 1, $\varepsilon_p$ and $\varepsilon_m$ denote dielectric permittivities of the particle and the medium, respectively. The parameters g and Γ$_R$ may be expressed by Equations 2 and 3 below.

$$g = -\alpha f^2(r)\omega_c / 2V_c \quad (2)$$

$$\Gamma_R = \alpha^2 f^2(r)\omega_c^4 / 6\pi v^3 V_c \quad (3)$$

In Equations 2 and 3, $\omega_c$ is the angular resonant frequency, f(r) designates normalized mode distribution, $V_c$ is the mode volume, and v=c/$\sqrt{\varepsilon_m}$ with c representing the speed of light.

Particle size may be derived from Equation 4 below.

$$\alpha = -(3\lambda^3/8\pi^2)(\Gamma_R/g) \quad (4)$$

Because the value of Γ$_{R/g}$ is independent of the particle position r on the resonator, this technique has advantages over schemes using resonance spectral shift, which is affected by particle positions. If $\varepsilon_p$>$\varepsilon_m$, the symmetric mode experiences a red-shift. If $\varepsilon_p$<$\varepsilon_m$, the symmetric mode experiences a blue-shift. In exemplary embodiments, $\varepsilon_p$>$\varepsilon_m$ is always satisfied, and a low-Q mode (an SM) therefore appears on the lower frequency side of the transmission spectrum.

More specifically, in one embodiment the radius of a particle is determined using Equation 5 below.

$$R = \left[\frac{(3\lambda^2/8\pi^2)((\gamma_1 - \gamma_2)/\delta)}{4\pi(n_p^2 - 1)/(n_p^2 + 2)}\right]^{\frac{1}{3}} \quad (5)$$

In Equation 5, $n_p$ denotes the refractive index of the particle. Given n=$\sqrt{\varepsilon\mu}$, in which μ, the relative permeability of the particle, is approximately equal to 1, $n_p^2$ is approximately equal to $\varepsilon_p$.

In exemplary embodiments, microtoroidal WGM resonator 200 has a quality value (Q) of approximately 4×10$^8$. A theoretical lower limit of measurable nanoparticle radius R may be estimated using 2g>Γ$_R$+$\omega_c$/Q. For example, at λ=670 nm, a radius of approximately 9.2 nm may be determined for potassium chloride (KCl), and a radius of approximately 8.7 nm may be determined for polystyrene.

Figure 6:
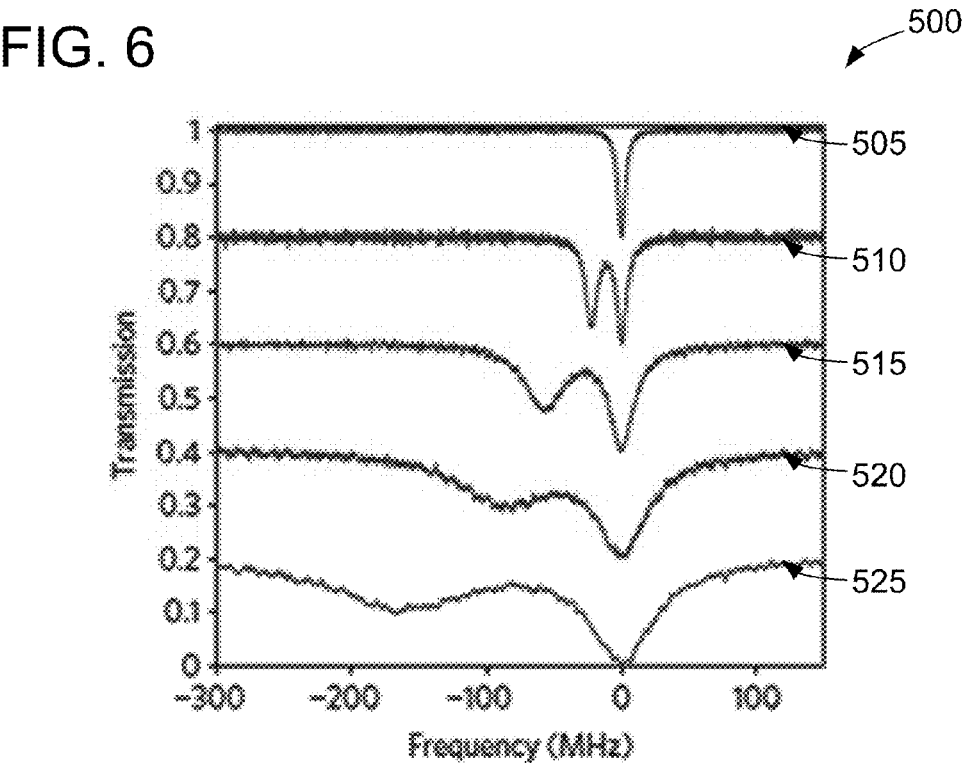
FIG. 6 is a chart illustrating example transmission spectra based on light coupled out of a passive WGM resonator when in the presence of varying quantities of particles.

FIG. 6 is a chart 500 illustrating example transmission spectra based on light coupled out of WGM resonator 102 in the presence of varying quantities of particles. A zero-particle transmission spectrum 505 depicts only a single mode, which represents two degenerate modes within WGM resonator 102, as described above. A one-particle transmission spectrum 510 depicts a splitting of the degenerate modes into two distinct modes separated by a relatively small distance and having relatively small linewidths.

Consecutive particle depositions on WGM resonator 102 affect both the distance between modes and the linewidths of the modes, as shown by a two-particle transmission spectrum 515, a three-particle transmission spectrum 520, and a four-particle transmission spectrum 525. The distance between the modes and the linewidths of the modes may be used to determine a quantity of nanoparticles. Although the progression from one-particle transmission spectrum 510 to four-particle transmission spectrum 525 indicates an increase in both distance and linewidths, the presence of an additional particle may instead result in a decrease in distance and/or linewidth(s), as described with regard to FIG. 7 below.

Figure 7:
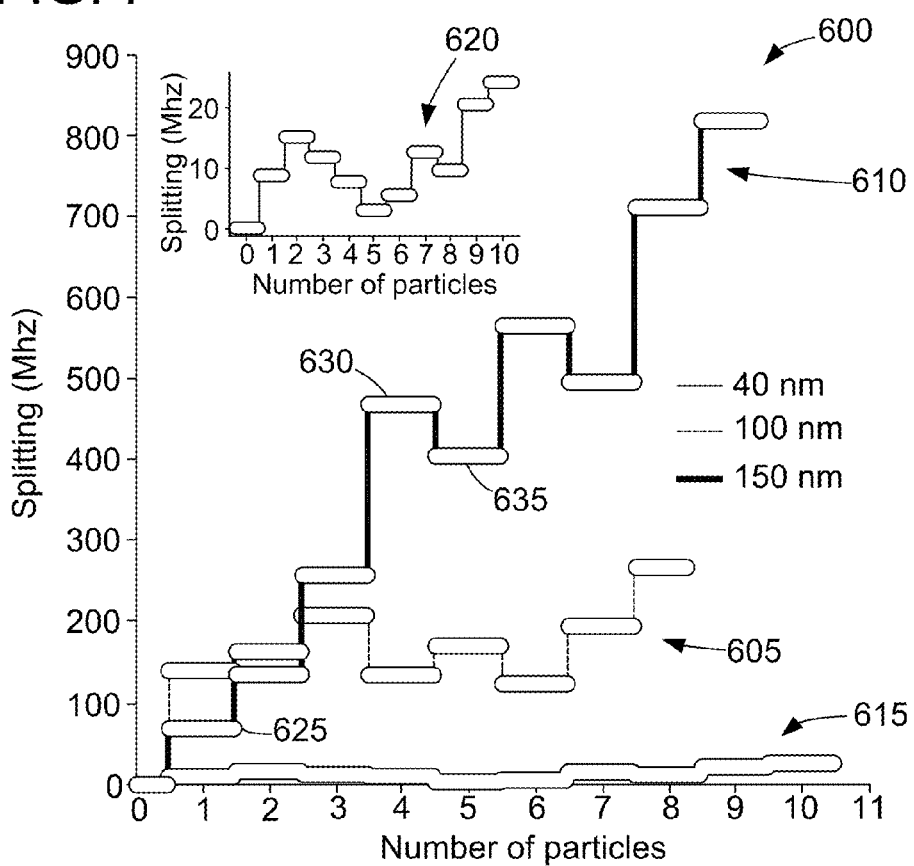
FIG. 7 is a chart illustrating distances between modes in example transmission spectra based on light coupled out of a passive WGM resonator when in the presence of varying quantities of particles.

FIG. 7 is a chart 600 illustrating distances between modes ("splitting") in example transmission spectra based on light coupled out of WGM resonator 102 in the presence of varying quantities of particles. More specifically, chart 600 illustrates splitting by both particle size and quantity of particles. Chart 600 includes a 150-nanometer (nm) line 605, a 100-nm line 610, and a 40-nm line 615. 40-nm line 615 indicates relatively small changes in splitting based on quantity of particles. A high-resolution 40-nm line 620 depicts discrete splitting levels for varying quantities of 40-nm particles.

Referring to 150-nm line 605, a continual increase in splitting is apparent between a one-particle splitting level 625 and a four-particle splitting level 630. This trend is consistent with the transmission spectra illustrated in FIG. 6. However, a five-particle splitting level 635 indicates a decrease in splitting compared to four-particle splitting level 630. In one embodiment, the splitting level depends on the location of a successively deposited particle with respect to the distribution of the SM and ASM, as shown in FIG. 5. Regardless of whether the addition of a particle increases or decreases splitting, detection of a particular level of splitting and/or a detection of a change in the level of splitting may be used to determine a quantity of and/or one or more properties of nanoparticles.

In some embodiments, mode splitting directly reveals particle polarizability, which depends at least in part on particle size and refractive index. Accordingly, a nanoparticle property (e.g., size, refractive index, or composition) may be determined based on mode splitting and a known value for one or more other properties. For example, nanoparticles with the same size but different composition may be discriminated. Embodiments providing such property determinations facilitate classifying biomolecules, for example.

Figure 8:
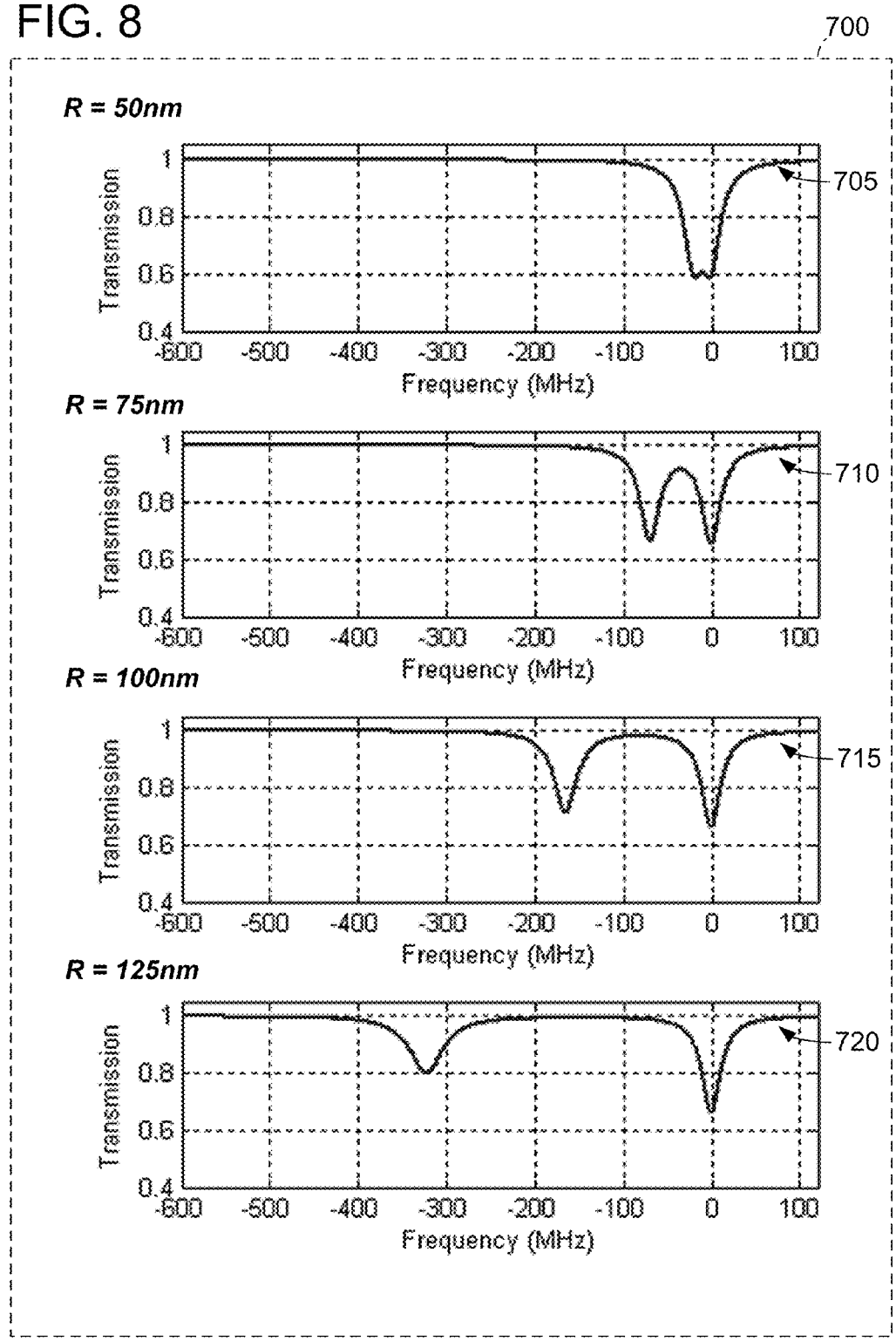
FIG. 8 is an illustration of example transmission spectra based on light coupled out of a passive WGM resonator in the presence of nanoparticles of varying sizes.

FIG. 8 is an illustration of example transmission spectra 700 based on light coupled out of WGM resonator 102 in the presence of nanoparticles of varying sizes. Depicted in FIG. 8 are a 50-nm transmission spectrum 705, a 75-nm transmission spectrum 710, a 100-nm transmission spectrum 715, and a 125-nm transmission spectrum 720. Nanometer measurements correspond to particle size, expressed as a radius length. The refractive index $n_p$ is constant at 1.48, and the normalized mode distribution f(r) is constant at 0.3.

50-nm transmission spectrum 705 includes split modes at a very small distance (i.e., approximately 20 Hertz (Hz)) from each other. As the particle size increases, the distance between the modes also increases. For example, 50-nm transmission spectrum 705 depicts a distance of approximately 20 MHz between the split modes, whereas 125-nm transmission spectrum 720 depicts a distance of approximately 320 MHz between the split modes. Because the level of mode splitting varies with radius R, a particle size may be determined based at least in part on the distance between the split modes.

Figure 9:
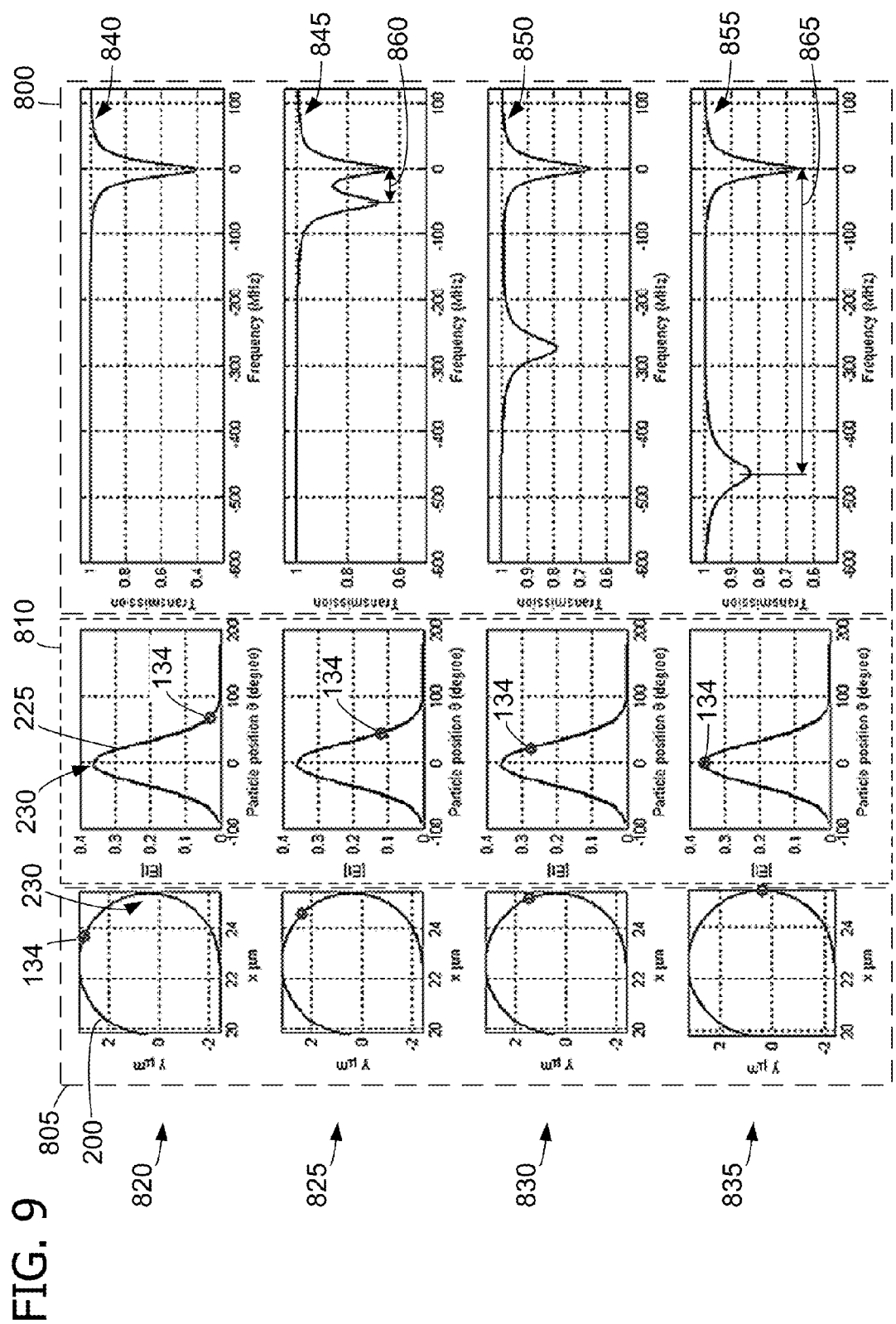
FIG. 9 is an illustration of example transmission spectra based on light coupled out of a passive microtoroidal WGM resonator in the presence of a nanoparticle at various positions relative to a WGM evanescent field.

FIG. 9 is an illustration of example transmission spectra 800 based on light coupled out of microtoroidal WGM resonator 200 in the presence of object 134 at various positions relative to a WGM evanescent field 225. Nanoparticle refractive index $n_p$ is constant at 1.48, and normalized mode distribution f(r) is constant at 0.3.

Physical position charts 805 illustrate the position of object 134 relative to the surface of microtoroidal WGM resonator 200. Field position charts 810 illustrate the position of object 134 relative to WGM evanescent field 225, which is most pronounced near center 230. Evanescent field center 230 corresponds to a right-most portion of physical position charts 805 and a peak of field position charts 810. Transmission spectra 800 are generated based on light coupled out of microtoroidal WGM resonator 200.

Physical position charts 805, field position charts 810, and transmission spectra 800 are provided for a first scenario 820, a second scenario 825, a third scenario 830, and a fourth scenario 835. In first scenario 820, object 134 is positioned almost completely outside evanescent field 225. In fourth scenario 835, object 134 is positioned at evanescent field center 230. In second scenario 825 and third scenario 830, object 134 resides at intermediate positions within evanescent field 225.

A first transmission spectrum 840 indicates that in first scenario 820, in which object 134 is mostly removed from evanescent field 225, mode splitting is not apparent. As indicated by a second transmission spectrum 845, a third transmission spectrum 850, and a fourth transmission spectrum 855, mode splitting increases as object 134 approaches evanescent field center 230. For example, second transmission spectrum 845 indicates a distance 860 of approximately 50 Hz between modes, whereas fourth transmission spectrum 855 indicates a distance 865 of approximately 465 Hz between modes. Because mode splitting varies with position, a position of object 134 may be determined based at least in part on the amount of mode splitting.

Figure 10:
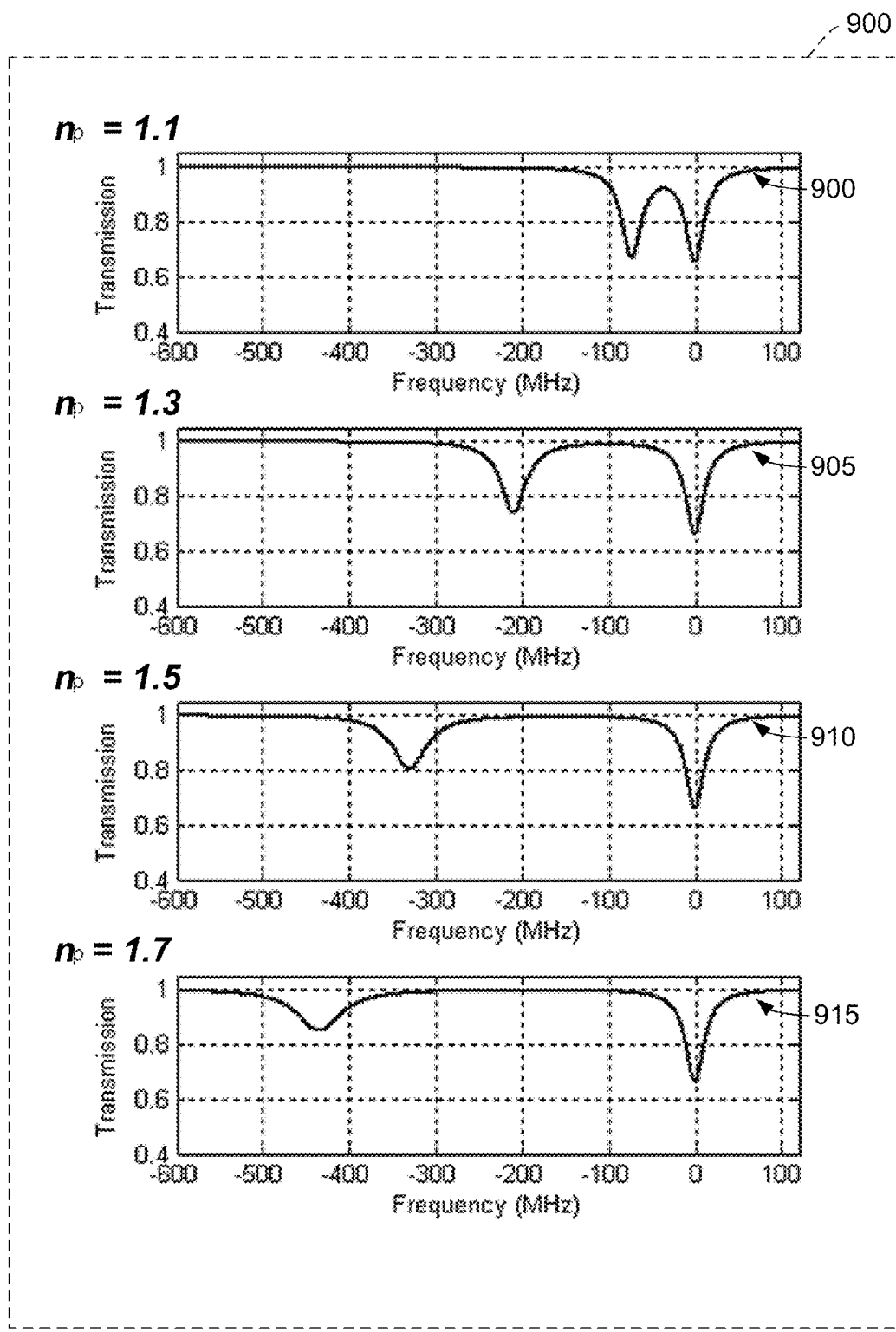
FIG. 10 is an illustration of example transmission spectra based on light coupled out of a passive WGM resonator in the presence of nanoparticles having varying refractive indices.

FIG. 10 is an illustration of example transmission spectra 900 based on light coupled out of WGM resonator 102 in the presence of nanoparticles having varying refractive indices. Nanoparticle radius R is constant at 125 nm, and normalized mode distribution f(r) is constant at 0.3.

A first transmission spectrum 905 corresponds to a nanoparticle having a refractive index $n_p$ of 1.1. A second transmission spectrum 910 corresponds to a nanoparticle having a refractive index $n_p$ of 1.3. A third transmission spectrum 915 corresponds to a nanoparticle having a refractive index $n_p$ of 1.5. A fourth transmission spectrum 920 corresponds to a nanoparticle having a refractive index $n_p$ of 1.7. As indicated by transmission spectra 905, 910, 915, 920, mode splitting varies with refractive index. Specifically, in the example of FIG. 10, mode splitting varies directly with refractive index. Because of the relationship between mode splitting and refractive index, a refractive index may be determined based at least in part on a distance between modes.

Figure 11:
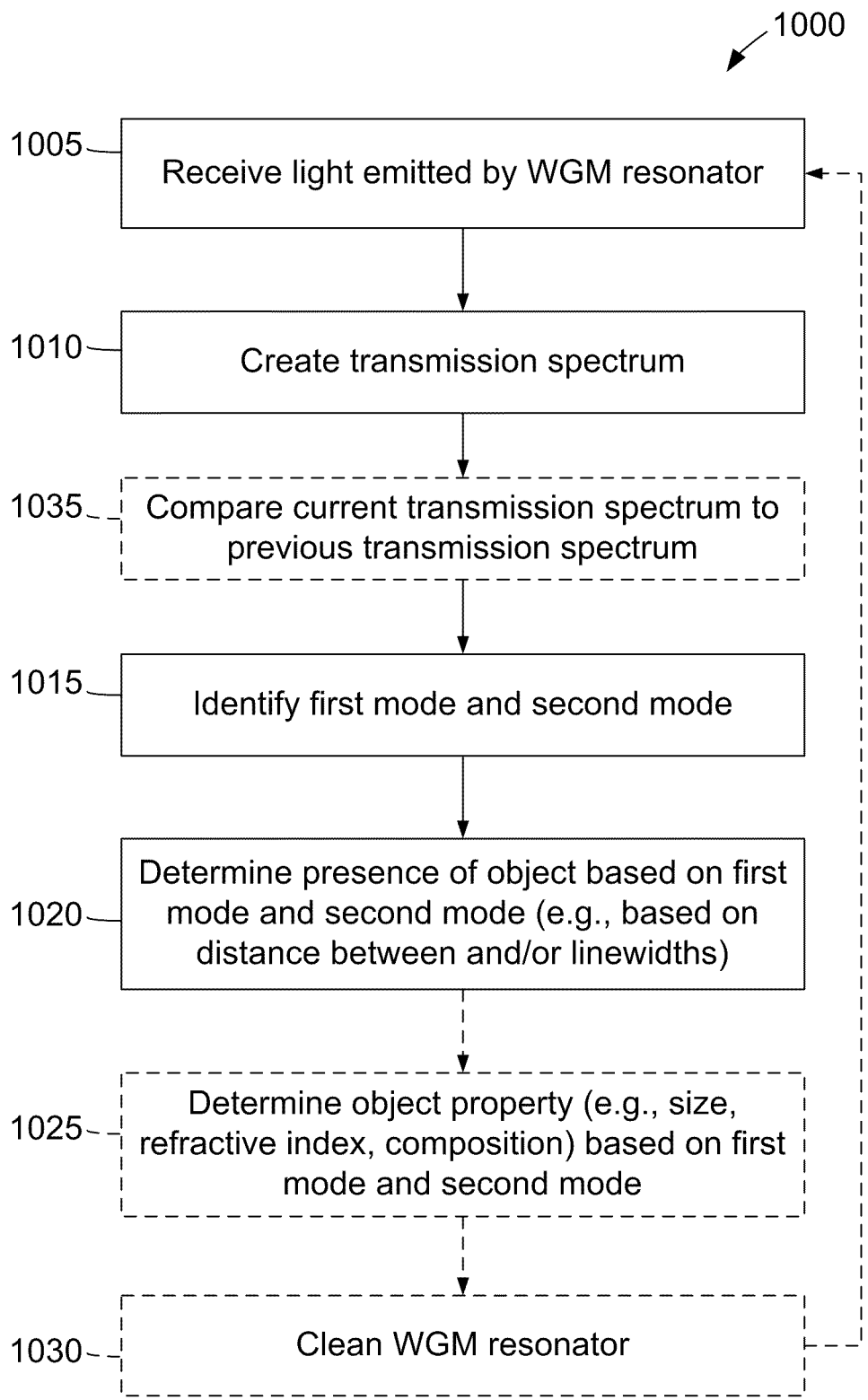
FIG. 11 is an example flow chart of a method for detecting an object based on mode splitting that may be used with a passive WGM resonator.

FIG. 11 is an example flow chart of a method 1000 for detecting an object based on mode splitting in a whispering gallery mode (WGM) resonator, such as WGM resonator 102. Method 1000 includes receiving 1005 light emitted by or coupled out of a WGM resonator. The light may be received via a photodetector. In one embodiment, light is received 1005 from an optical fiber configured to transmit the light emitted by or coupled out of the WGM resonator. For example, the optical fiber and WGM resonator may be arranged as shown in FIGS. 1-3.

A transmission spectrum is created 1010 based on the received light. A first mode and a second mode are identified 1015 within the transmission spectrum. The first mode and the second mode represent portions of the transmission spectrum associated with decreased transmission.

A presence of an object (e.g., a virion or nanoparticle) adsorbed on the WGM resonator and/or within an evanescent field of the WGM resonator is determined 1020 by a processor based on the first mode and the second mode. For example, the presence of the object may be determined 1020 based on a distance between the first mode and the second mode and, optionally, a linewidth of the first mode and/or a linewidth of the second mode.

In addition, or alternatively, one or more object properties, such as size, refractive index, and/or composition, may be determined 1025 based on the first mode and the second mode. For example, an object property may be determined based on a distance between the first mode and the second mode, a linewidth of the first mode, and/or a linewidth of the second mode.

In some embodiments, the WGM resonator is cleaned 1030 after detection of object presence and/or properties. Hydrophilic or water (solvent)-soluble particles, such as potassium chloride (KCl), may be removed by condensing water vapor on the surface of the WGM resonator and then by drying the surface with dry air or nitrogen. Hydrophobic or insoluble particles may be removed by steam laser cleaning; by high-speed steam and purified water droplet cleaning; by high-velocity aerosol cleaning with ultrapure water and/or a dilute aqueous solution; by applying solid argon, a nitrogen aerosol, or a $CO_2$ aerosol; or by dry laser cleaning.

After determining 1020 a presence of an object, determining 1025 a property of an object, and/or or cleaning 1030 the WGM resonator, method 1000 may be repeated. In some embodiments, a current transmission spectrum is created 1010 and compared 1035 to a previous transmission spectrum. For example, the previous transmission spectrum may be subtracted from the current transmission spectrum to create a difference. The first mode and the second mode may be identified 1015 based on the comparison (e.g., based on the difference). In addition, or alternatively, an object presence and/or an object property may be determined 1020, 1025 based on the comparison.

Active WGM Resonator

Referring to FIG. 1, in some embodiments, an active WGM resonator 102 includes or defines a cavity 235 that includes (e.g., is populated or doped with) a gain medium. In exemplary embodiments, the gain medium includes ions of one or more rare earth metals, such as erbium (Er), neodymium (Nd), or ytterbium (Yb), and/or other types of light emitters including quantum dots.

In such embodiments, light source 112 includes a pump light with a wavelength that overlaps with the absorption band of the gain medium and is used to pump the gain medium. A tunable wavelength may not be required for light source 112.

The power of light from light source 112 is adjusted above a lasing threshold associated with the gain medium in WGM resonator to achieve a lasing effect. Normally, the lasing effect produces a laser mode (e.g., light within a relatively narrow linewidth) at a frequency that is different from the frequency of output from light source 112. When an object is proximate to (e.g., adsorbed on) WGM resonator 102, the laser mode is split into two modes.

Some residual light from pump light source 112 may exist in the light coupled out of WGM resonator 102. Accordingly, in some embodiments, detection device 104 includes a wavelength-division multiplexer (WDM) 109 that is configured to receive the light coupled out of WGM resonator 102 and to separate the lasing light from the residual pump light, creating filtered light. The filtered light is passed to photo detector 106. In other embodiments, WDM 109 is omitted.

Photodetector 106 is configured to receive the light emitted by WGM resonator 102 (optionally filtered by WDM 109) and to combine the split laser modes that are included in the received light to create a heterodyne beat signal. Processor 108 is programmed to determine a beat frequency based on the heterodyne beat signal and to detect the presence of an object based on the beat frequency.

In exemplary embodiments, an active WGM resonator 102 and light source 112 (which may collectively be referred to as a "WGM microcavity laser") produce two frequency-degenerate but counter-propagating traveling laser modes: clockwise and counter-clockwise modes. The laser modes are highly confined with evanescent tails probing the surrounding medium many times during circulating within the cavity. A particle that enters the evanescent field of the cavity mode couples these two degenerate laser modes to each other via intracavity Rayleigh backscattering, and leads to the splitting of the laser frequency. This reflects itself as a transition from a single frequency lasing spectrum to a two-frequency lasing spectrum with the spectral distance between the two laser modes determined by the polarizability $\alpha$ (e.g., size and shape of the particle and its refractive index contrast with the surrounding medium) of the particle and by the location of the particle in the mode volume. The polarizability of a spherical particle of radius R is given by Equation 1 above. Thus, a change in $\alpha$ of the particle may be translated into a change in the amount of frequency splitting. Similarly, a subsequent particle binding event may induce excess polarizability that will be observed as another change in the frequency splitting.

In exemplary embodiments, frequency splitting information is extracted by mixing the split modes at a photodetector of sufficient bandwidth to create a heterodyne beat note signal with a beat frequency corresponding to the frequency splitting. In such embodiments, single object adsorption events may be revealed in real time by monitoring the beat note signal and its frequency component.

Exemplary WGM microcavity lasers include toroidal cavities fabricated from Erbium (Er)-doped silica. Such resonators may have a diameter of 20-40 μm and may have quality factors (Q) of approximately $6 \times 10^6$. Further, an exemplary WGM microcavity laser includes a silica WGM resonator doped with Er ions at a concentration of approximately $5 \times 10^{18}$ ions/cm$^3$. Such a concentration facilitates continuous-wave (CW) laser operation.

The resonator is continuously pumped by a CW laser diode with a wavelength of 1.46 μm, which lies within the Er absorption band. A lasing effect is produced within WGM resonator, producing from the input light a laser emission in the 1.55 μm band. This laser emission is monitored by a photodiode.

Figure 12:
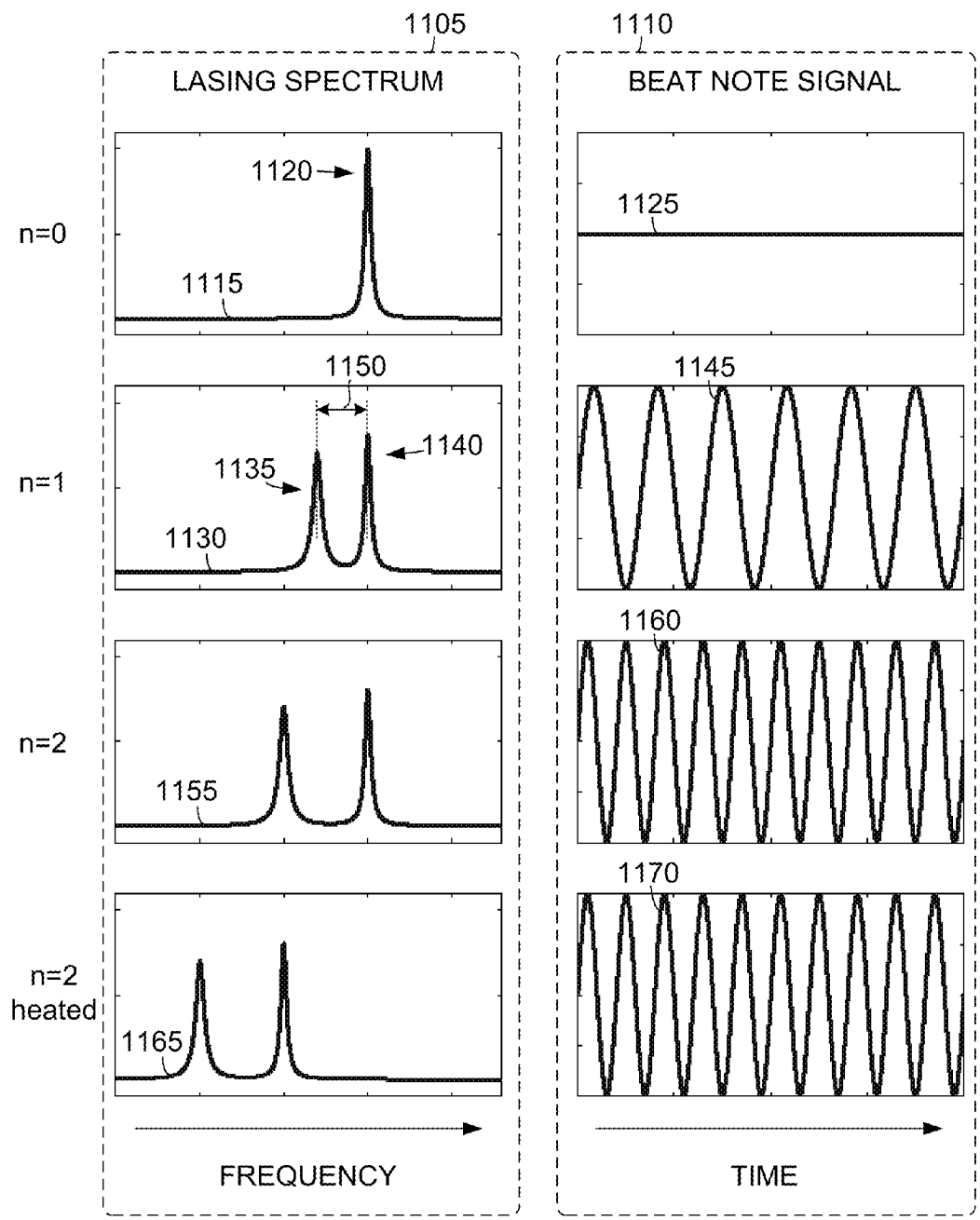
FIG. 12 is an illustration of example lasing spectra and heterodyne beat signals based on light coupled out of an active WGM resonator when in the presence of varying quantities of nanoparticles.

FIG. 12 is an illustration of example lasing spectra 1105 and heterodyne beat signals 1110 based on light coupled out of an active WGM resonator when in the presence of varying quantities of nanoparticles. In the absence of a nanoparticle, a zero-particle lasing spectrum 1115 is produced, with a single laser mode 1120. A corresponding zero-particle heterodyne beat signal 1125 represents constant laser intensity, or a beat frequency of zero.

When a first particle is present, the laser mode splits. A one-particle lasing spectrum 1130 includes a first laser mode 1135 and a second laser mode 1140. A corresponding one-particle heterodyne beat signal 1145 fluctuates with a beat frequency that corresponds to the amount of frequency splitting (e.g., a distance 1150 between first laser mode 1135 and second laser mode 1140).

Subsequent particle adsorption events further change the observed beat frequency. For example, a two-particle lasing spectrum 1155 indicates an increase in mode splitting, and a corresponding two-particle heterodyne beat signal 1160 represents a higher beat frequency than is shown in one-particle heterodyne beat signal 1145. In exemplary embodiments, because the split laser modes reside in the same microcavity, environmental noise, such as a temperature fluctuation, affects both modes in the same way. Accordingly, although each split mode undergoes a spectral shift, as indicated by a heated two-particle lasing spectrum 1165, the amount of frequency splitting and, therefore, the beat frequency, does not change. For example, a heated two-particle heterodyne beat signal 1170 is equal to two-particle heterodyne beat signal 1160. Such embodiments enable detecting objects with an apparatus that is largely resistant to environmental noise.

Figure 13:
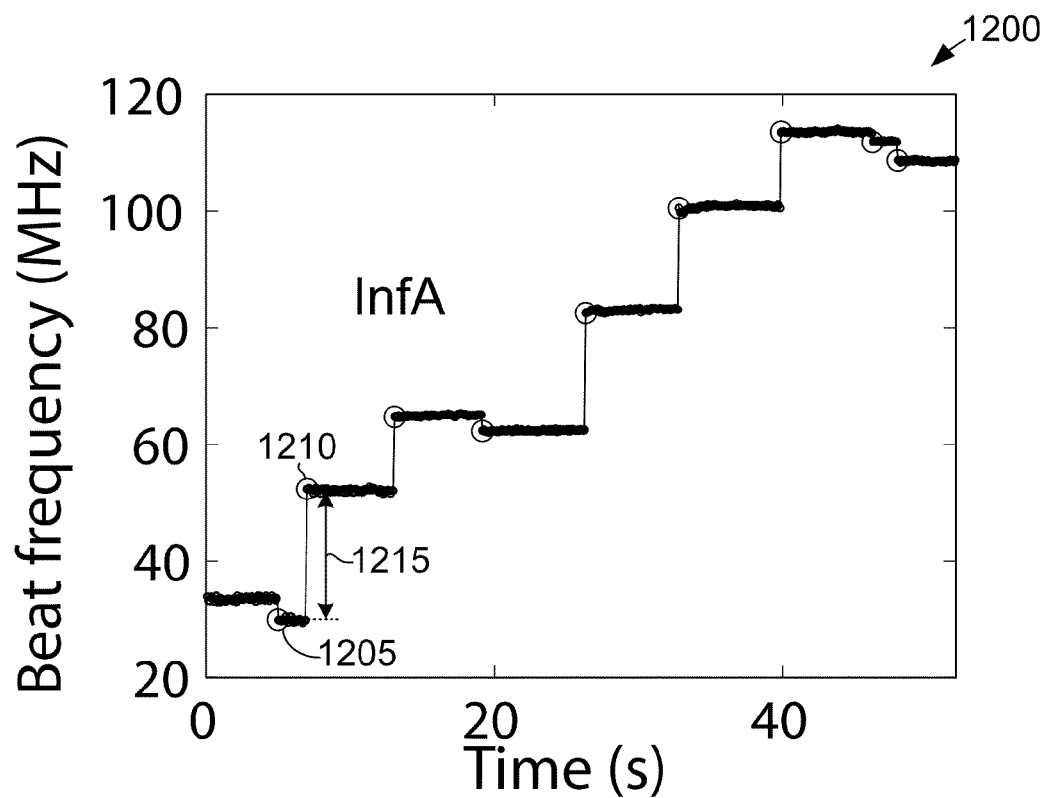
FIG. 13 is a chart illustrating example beat frequencies based on light coupled out of an active WGM resonator in the presence of varying quantities of Influenza A (InfA) virions.

FIG. 13 is a chart 1200 illustrating example beat frequencies based on laser emitted from an active WGM resonator in the presence of varying quantities of Influenza A (InfA) virions. In chart 1200, each discrete upward or downward change in the beat frequency corresponds to a single virion adsorption event, also referred to as a binding event. A first point 1205 represents the adsorption of a first particle, and a second point 1210 represents the adsorption of a second particle. A positive change 1215 in the beat frequency is shown between first point 1205 and second point 1210. The heights and the signs (e.g., positive or negative) of the changes in the beat frequency are related to the polarizability of each arriving particle and to the location of each particle with respect to the previously adsorbed particles in the field distribution of the laser modes.

Aside from the incorporation of a gain medium, the structure of an active WGM resonator may be similar to the structure of a passive WGM resonator. Accordingly, in some embodiments, an active WGM resonator is represented by WGM resonator 200 shown in FIG. 3. As indicated by Wgm evanescent field 225, the optical field on the surface of WGM resonator 200 is non-uniform, such that the light-matter interaction strength varies depending on the position of a particle on WGM resonator 200. Consequently, a single particle adsorbed in different locations in the mode volume induces different amount of frequency splitting.

In exemplary embodiments, when individual polystyrene (PS) nanoparticles of the same size are adsorbed onto WGM resonator 200 at random locations, the resultant frequency splitting either increases or decreases with different step heights. For an ensemble of particles with the same polarizability adsorbed one by one onto the microcavity laser, the beat frequency steps are not constant. Instead, the beat frequency steps form a statistical distribution with a standard deviation that scales linearly with particle polarizability. Such results have been verified with a Monte Carlo simulation in which PS nanoparticles were continuously and randomly deposited in a microcavity mode volume. In the simulation, the PS particles had a radius R=50 nanometers (nm) and refractive index $n_p$=1.59. The zero-particle light emission from the resonator had a wavelength λ=1550 nm. The surrounding medium was air, with a refractive index $n_s$=1.0. The resonator had a mode volume V=300 µm³. In such a simulation, each nanoparticle adsorption event leads to an upward or downward change in the frequency splitting. The step height of each change depends on the particle location in the mode volume. Nanoparticles with smaller size lead to a narrower distribution of step changes. Because the polarizability is proportional to $R^3$, the size of the particles with a known refractive index can be estimated by proper calibration using particles of known size.

Figure 14:
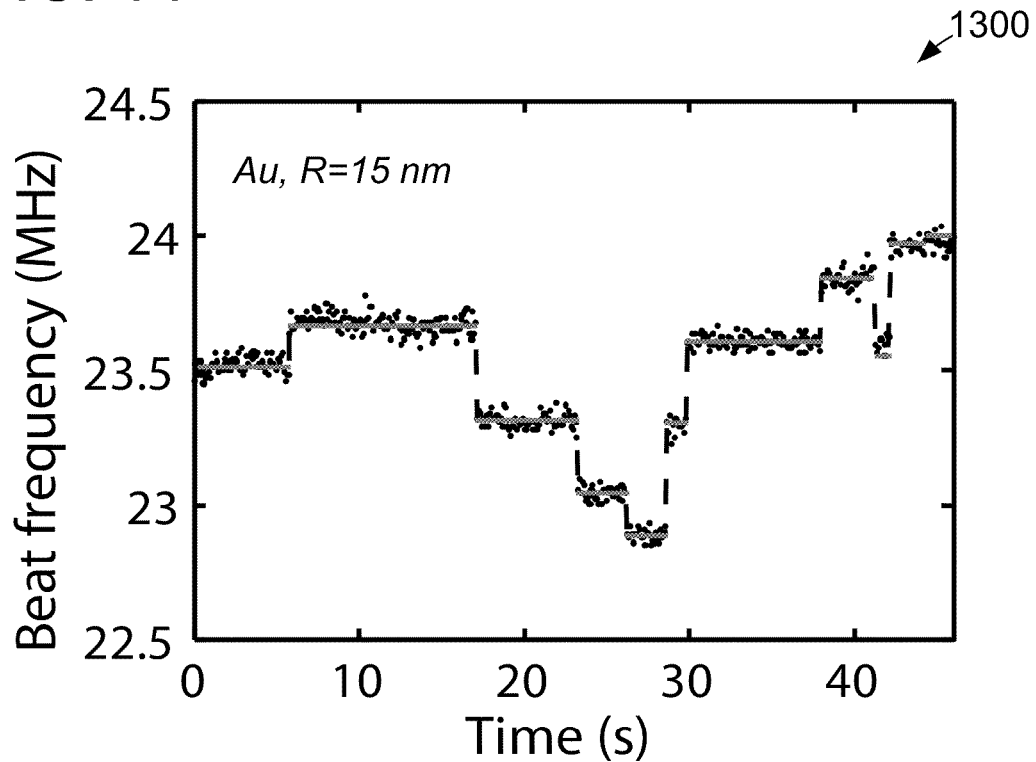
FIG. 14 is a chart illustrating example beat frequencies based on light coupled out of an active WGM resonator in the presence of varying quantities of gold nanoparticles with a radius of 15 nanometers.
Figure 15:
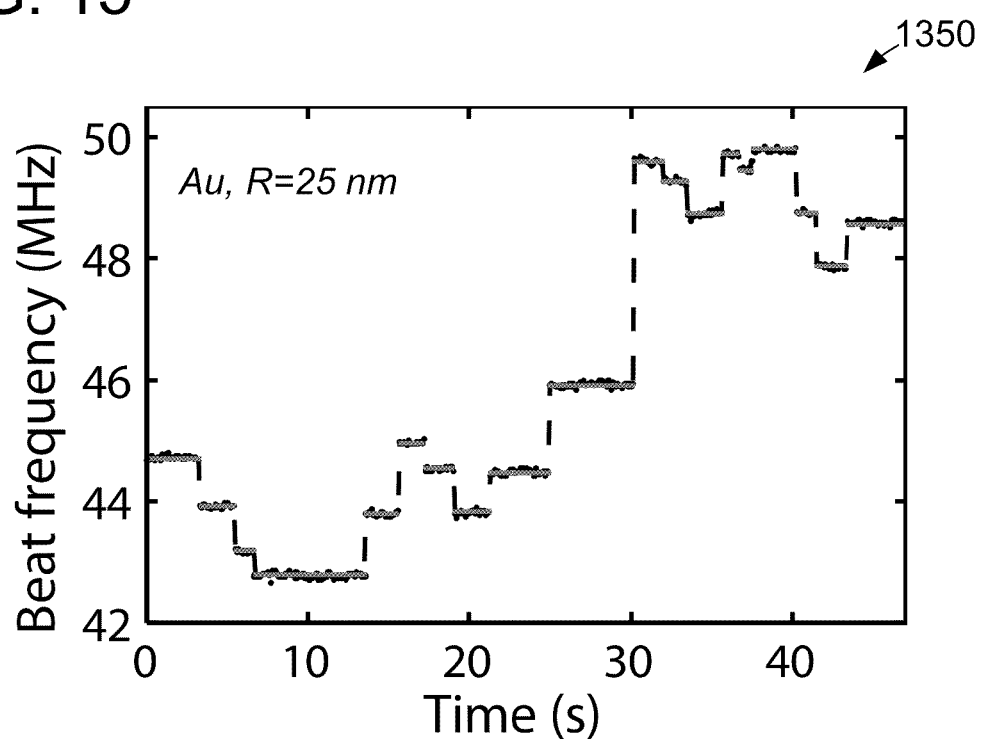
FIG. 15 is a chart illustrating example beat frequencies based on light coupled out of an active WGM resonator in the presence of varying quantities of gold nanoparticles with a radius of 25 nanometers.

FIG. 14 is a chart 1300 illustrating example beat frequencies based on the laser emitted from an active WGM resonator in the presence of varying quantities of gold (Au) nanoparticles with a radius of 15 nm. FIG. 15 is a chart 1350 illustrating example beat frequencies based on the laser emitted from an active WGM resonator in the presence of varying quantities of Au nanoparticles with a radius of 25 nm. In chart 1300 and chart 1350, particles are individually deposited at random locations on the surface of the microcavity laser. The measurements of beat frequency were performed using the same microcavity laser and the same laser mode to minimize cavity- and mode-related effects. As shown by chart 1300, changes in beat frequency are apparent as Au particles are individually adsorbed to the active WGM resonator, even with a radius of only 15 nm.

Figure 16:
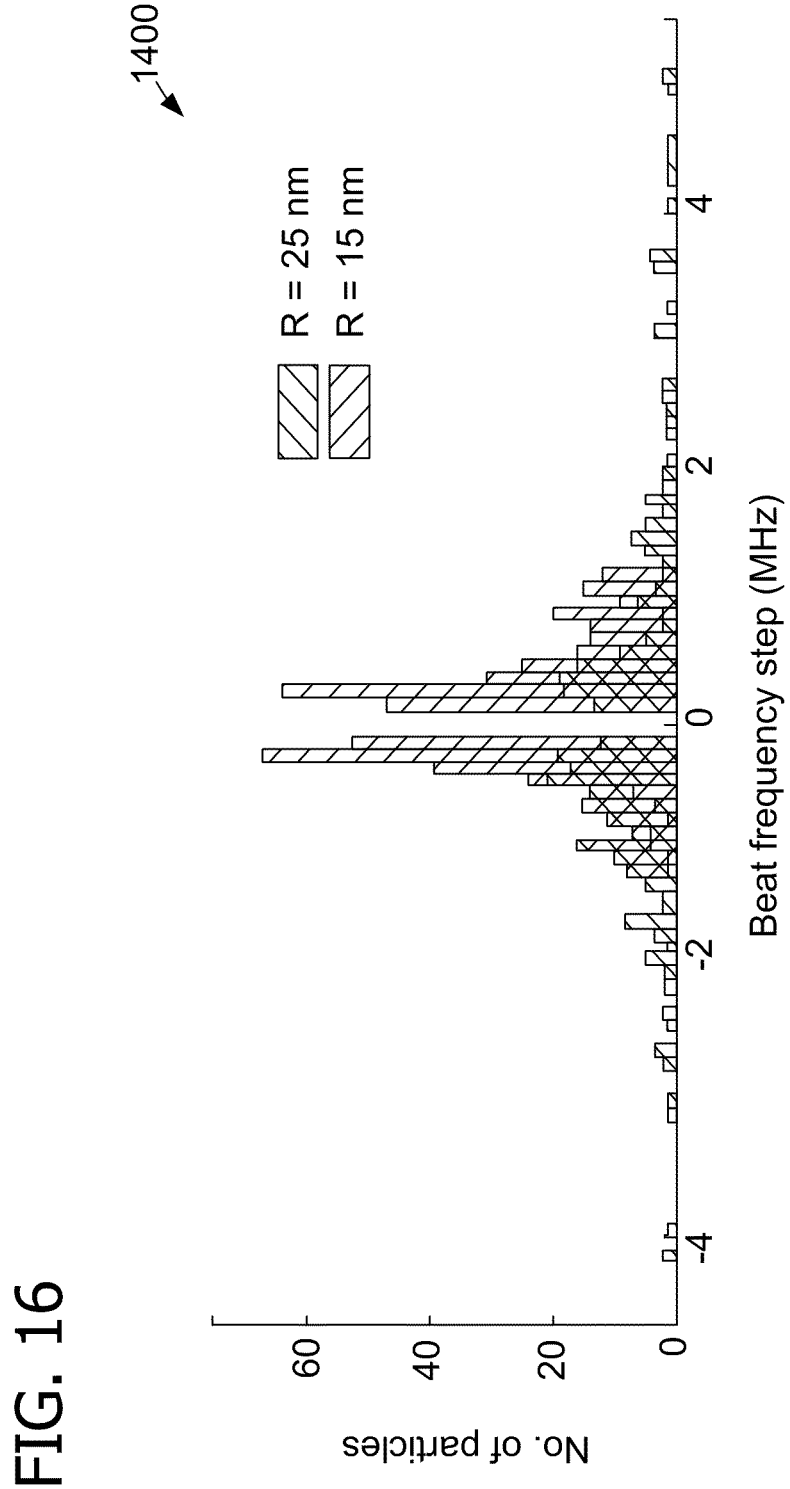
FIG. 16 is a histogram illustrating example changes in beat frequency versus the number of binding events for gold particles with radii of 15 nanometers and 25 nanometers.

FIG. 16 is a histogram 1400 illustrating example changes in beat frequency versus the number of binding events for gold particles with radii of 15 nanometers and 25 nanometers. Histogram 1400 indicates binding events for a total of 816 Au nanoparticles, measured using the same active WGM resonator and the same laser mode. More specifically, 397 binding events are illustrated for R=15 nm, and 419 binding events are illustrated for R=25 nm. In exemplary embodiments, small nanoparticles do not cause significant change in the cold cavity-Q and the linewidth of the laser mode.

As indicated by histogram 1400, the standard deviation for R=25 nm (e.g., as shown in FIG. 15) is larger than the standard deviation for R=15 nm (e.g., as shown in FIG. 14). Accordingly, the standard deviation of beat frequency changes may be used to extract the polarizability of particles and, therefore, the size of an unknown particle by using measurements associated with reference particles.

In exemplary embodiments, linewidth broadening of the laser modes due to the losses induced by nanoparticles of R<250 nm is significantly less than the induced frequency splitting between the laser modes. Therefore, such embodiments facilitate detecting a relatively large quantity of binding events using the same laser mode in a single microcavity laser without significantly degrading the lasing linewidth.

Embodiments described above detect particle binding events using a microcavity laser that produces a single laser mode. In some embodiments, a microcavity laser produces multiple laser modes.

Figure 17:
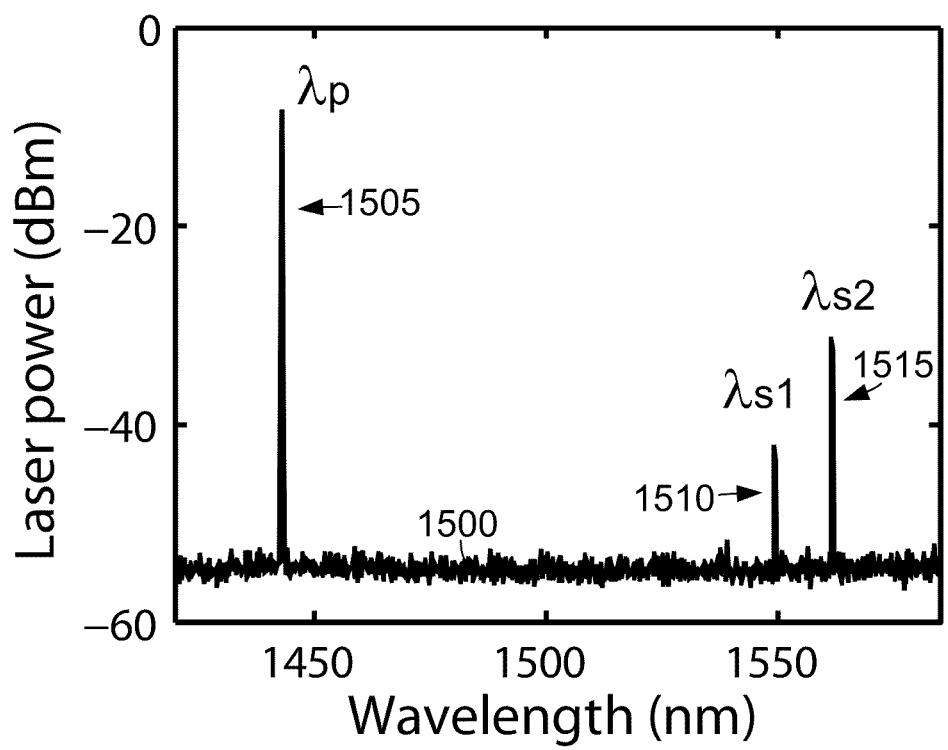
FIG. 17 is an illustration of an example lasing spectrum based on light coupled out of a two-mode active WGM resonator.

FIG. 17 is an illustration of an example lasing spectrum 1500 based on a laser emitted from a two-mode active WGM resonator. Lasing spectrum 1500 illustrates input light 1505 pumped at a wavelength $λ_p$=1443 nm. A first laser mode 1510 is illustrated at a first lasing wavelength $λ_{s1}$=1549 nm, and a second laser mode 1515 is illustrated at a second lasing wavelength $λ_{s2}$=1562 nm.

Figure 18:
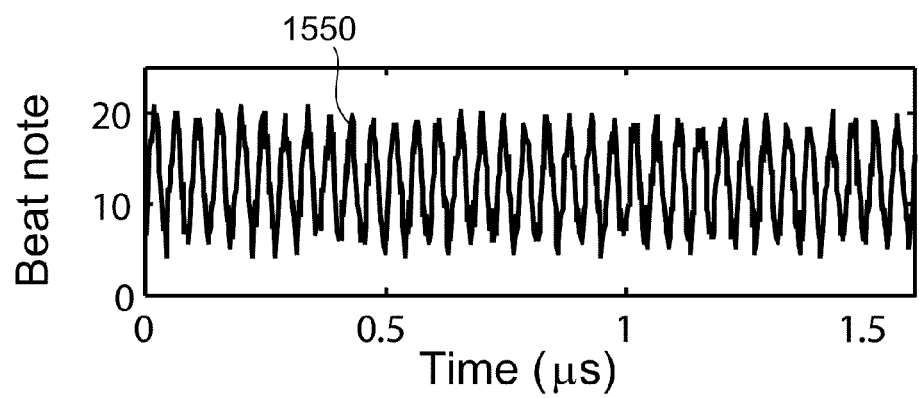
FIG. 18 is an illustration of an example heterodyne beat signal based on light coupled out of a two-mode active WGM resonator in the presence of one or more particles.

When a particle is adsorbed onto the two-mode active WGM resonator, first laser mode 1510 and/or second laser mode 1515 splits, as described above, and a heterodyne beat signal can be created from the split modes. When both first laser mode 1510 and second laser mode 1515 split, a total of four laser modes may be present in the light emitted by the active WGM resonator. FIG. 18 is an illustration of an example heterodyne beat signal 1550 based on the laser emitted from a two-mode active WGM resonator in the presence of one or more particles.

Figure 19:
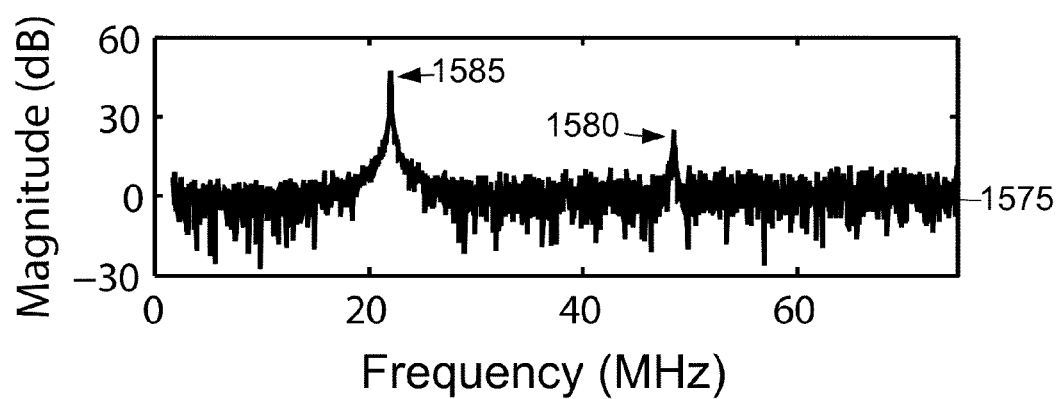
FIG. 19 is an illustration of a fast Fourier transform (FFT) spectrum based on the heterodyne beat signal shown in FIG. 18.

In exemplary embodiments, a fast Fourier transform (FFT) is applied to a heterodyne beat signal, such as heterodyne beat signal 1550, to determine one or more beat frequencies. FIG. 19 is an illustration of a fast Fourier transform spectrum 1575 based on heterodyne beat signal 1550. Referring to FIGS. 17 and 18, a first peak 1580 and a second peak 1585 in FFT spectrum 1575 correspond to frequency splitting in the first laser mode 1510 and the second laser mode 1515, respectively.

Figure 20:
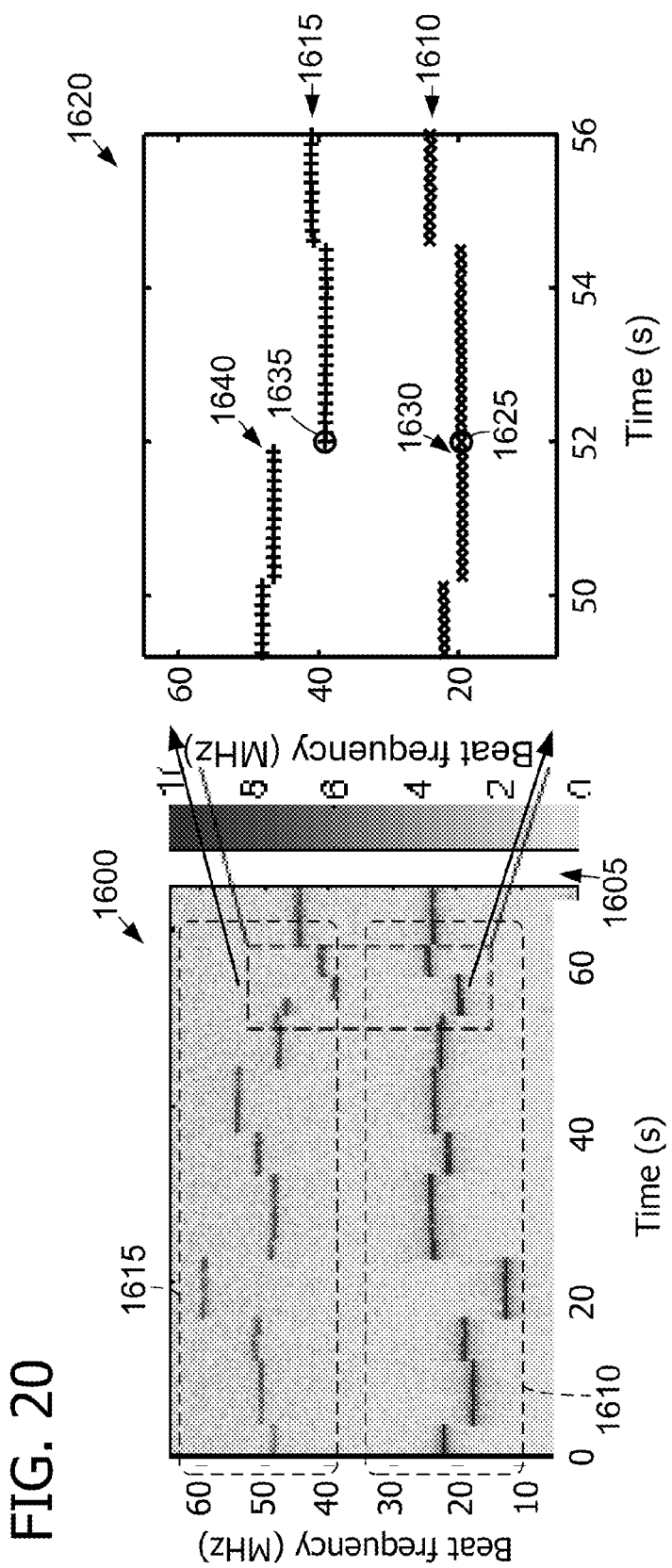
FIG. 20 is an illustration of an intensity graph 1600 based on an FFT spectrum as gold particles are deposited onto the surface of an active WGM resonator.

FIG. 20 is an illustration of an intensity graph 1600 based on an FFT spectrum, such as FFT spectrum 1575 (shown in FIG. 19), as gold particles with a radius R=50 nm are deposited onto the surface of an active WGM resonator. A sidebar 1605 indicates the magnitude of FFT spectrum 1575 in decibels (dB).

Referring to FIGS. 19 and 20, a first beat frequency group 1610 corresponds to first peak 1580, and a second beat frequency group 1615 corresponds to second peak 1585. As described above with reference to FIG. 13, changes in the beat frequency within a group over time indicate binding events. As shown in intensity graph 1600, beat frequency changes for first beat frequency group 1610 and second beat frequency group 1615 differ for the same binding events (e.g., events occurring at the same time).

An expanded view of a portion of intensity graph 1600 is shown in a close-up graph 1620. A first beat frequency point 1625 represents a binding event that is not indicated by first beat frequency group 1610. More specifically, first beat frequency point 1625 is not vertically offset from preceding beat frequency points 1630. Conversely, a second beat frequency point 1635 is vertically offset from preceding beat frequency points 1640 in second beat frequency group 1615. Accordingly, second beat frequency group 1615 indicates the binding event.

Embodiments in which a microcavity laser produces multiple laser modes enable redundant detection of binding events. In such embodiments, a binding event that does not significantly affect a first laser mode may significantly affect a second laser mode, such that the binding event may be detected.

More generally, embodiments including an active WGM resonator facilitate eliminating the need for a narrow linewidth tunable laser source to detect induced spectral shift and/or mode splitting, thus enabling a reduction in the cost of the detection system. Moreover, the use of an active WGM resonator and a pump light source may increase detection speed, as no tuning delay is incurred, and noise, such as thermal effects and piezo-motion, may be reduced or eliminated.

The split laser modes in an active WGM resonator reside in the same microcavity and are affected in the same way by the noise sources which affect the microcavity homogenously (e.g., environmental noise, the pump laser source, etc.). Accordingly, an active WGM resonator provides a self-referencing system. For example, while an arriving nanoparticle leads to a change in the amount of frequency splitting, changes in the environmental or the cavity temperature does not change the amount of frequency splitting but rather shift both modes consistently. Thus, high detection sensitivity, real-time and in-situ measurements may be facilitated without the need for active stabilization or temperature control.

Figure 21:
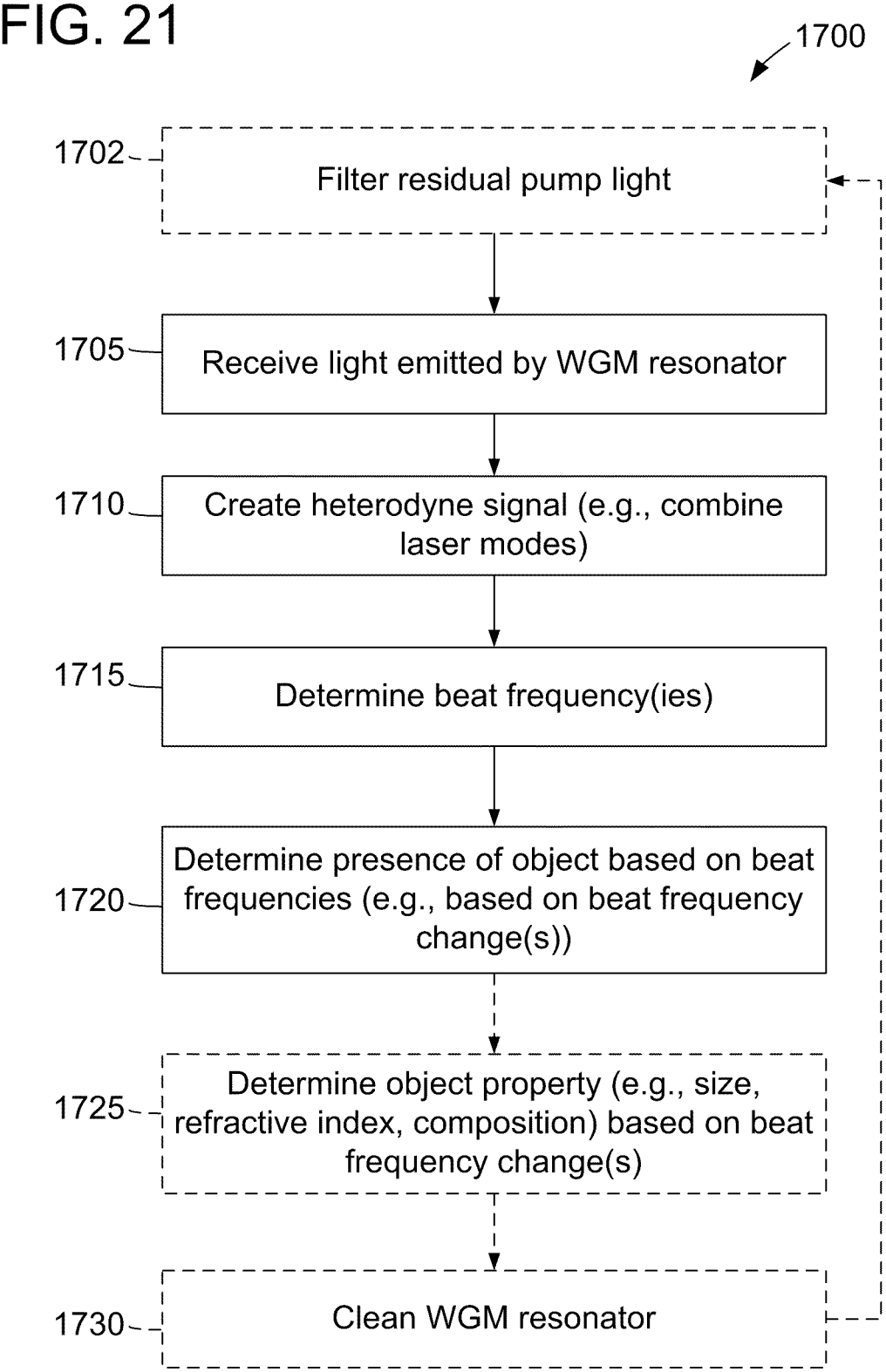
FIG. 21 is an example flow chart of a method for detecting a nanoparticle based on mode splitting that may be used with an active WGM resonator.

FIG. 21 is an example flow chart of a method 1700 for detecting an object based on mode splitting that may be used with an active WGM resonator. Method 1700 includes receiving 1705, by a photodetector, light emitted by a whispering gallery mode (WGM) resonator. The WGM resonator may be an active WGM resonator, doped with a gain medium. In exemplary embodiments, the received light includes a pair of split laser modes, with a first split laser mode representing light transmission in a first frequency range and a second split laser mode representing light transmission in a second frequency range.

In some embodiments, the light from the WGM resonator is filtered 1702 before it is received by the photodetector. In exemplary embodiments, the emitted light includes laser modes emitted by the WGM resonator based on light from a light source. The light is filtered 1702 by a wavelength-division multiplexer to reduce or remove residual light from the light source (e.g., light other than light corresponding to the laser modes), creating filtered laser light that is transmitted to the photodetector.

A heterodyne beat signal is created 1710 based on the received light. For example, the photodetector may create 1710 the heterodyne beat signal at least in part by combining the first split laser mode and the second split laser mode. In some embodiments, the WGM resonator produces a single initial laser mode in the absence of a particle and two split laser modes in the presence of one or more particles. In other embodiments, the WGM resonator produces two or more initial laser modes in the absence of a particle and a pair of split laser modes corresponding to each initial laser mode in the presence of one or more particles. For example, if the WGM resonator produces two initial laser modes and a total of four split laser modes, all four split laser modes may be combined to create 1710 the heterodyne beat signal.

One or more beat frequencies are determined 1715 by a processor based on the heterodyne beat signal. For example, the processor may apply a fast Fourier transform to the heterodyne beat signal to determine 1715 a beat frequency. In embodiments in which the WGM resonator produces multiple pairs of split laser modes, a plurality of beat frequencies may be determined 1715, with each beat frequency corresponding to a pair of split laser modes.

The presence of an object proximate to the WGM resonator is determined 1720 by the processor based on the beat frequency. For example, when the beat frequency is greater than zero, the presence of at least one object may be determined 1720. In some embodiments, method 1700 is performed repeatedly (e.g., continuously and/or periodically). Each iteration of method 1700 is associated with a time of execution, and the current beat frequency (e.g., determined 1715 at a current time) is compared to a previous beat frequency (e.g., determined 1715 at a previous time). The presence of an object is determined 1720 based on a comparison of the current beat frequency to the previous beat frequency. For example, if the current beat frequency does not equal (e.g., differs by more than 1%, 2%, or 5% from) the previous beat frequency, the presence of an additional object may be determined 1720.

In addition, one or more attributes (e.g., size, refractive index, and/or composition) of the object may be determined 1725. For example, the size of an object may be determined 1725 by monitoring the changes in both the amount of frequency splitting and linewidths of the split laser modes in the light received 1705 from the WGM resonator. This may be done by employing linewidth measurement techniques. In some embodiments, the WGM resonator is cleaned 1730, similar to cleaning 1030, as shown in FIG. 11, to remove objects from the WGM resonator.

Active WGM resonator embodiments facilitate an object (e.g., nanoparticle and/or virion) detection scheme using an on-chip WGM microcavity laser. Detection and counting of individual objects may be achieved by monitoring the changes in the heterodyne beat frequency of the split laser modes in the microcavity laser. Individual object depositions are resolved as discrete step changes in the frequency splitting of the laser mode. Histograms of the frequency splitting steps may be used to extract the size of objects. Although embodiments described herein involve the use of a microtoroidal cavity laser, the principles and detection scheme can be applied to any other WGM microcavity lasers and/or other WGM resonator systems. For example, the techniques described herein with regard to passive resonators and active resonators may be applied to an aqueous environment and/or any other environment for detecting single biomolecules and/or particles.

Embodiments described herein enable the detection of nanoscale objects using a microcavity laser. Such microcavity lasers produce a narrow laser linewidth and facilitate a self-referencing detection scheme. For example, given linewidths as narrow as 4 Hz have for lasing in Er-doped WGM microcavities, detection of frequency splittings as small as a few tens of Hz, which translates into a lower detection limit of R~0.5 nm, may be possible with WGM microcavity lasers.

While the making and use of various embodiments of the invention are discussed in detail above, the embodiments of the invention provide many applicable inventive concepts that may be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the embodiments of the invention. Terms such as "a," "an" and "the" are not intended to refer to only a singular entity, but include the general class of which a specific example may be used for illustration. The terminology herein is used to describe specific embodiments of the invention, but their usage does not delimit the invention, except as outlined in the claims.

The order of execution or performance of the operations in embodiments of the invention illustrated and described herein is not essential, unless otherwise specified. For example, it is contemplated that executing or performing a particular operation before, contemporaneously with, or after another operation is within the scope of aspects of the invention. Embodiments of the invention may include additional or fewer operations than those disclosed herein.

Exemplary Operating Environment

Collection and analysis of object detection data such as described herein is typically performed by a computer or computing device. A computer or computing device includes one or more processors or processing units, system memory, and some form of computer readable media. By way of example and not limitation, computer readable media comprise computer storage media and communication media. Computer storage media include volatile and nonvolatile, removable and non-removable media implemented in any method or technology for storage of information such as computer readable instructions, data structures, program modules or other data. Communication media typically embody computer readable instructions, data structures, program modules, or other data in a modulated data signal such as a carrier wave or other transport mechanism and include any information delivery media. Combinations of any of the above are also included within the scope of computer readable media.

Although described in connection with an exemplary computing system environment, embodiments of the invention are operational with numerous other general purpose or special purpose computing system environments or configurations. The computing system environment is not intended to suggest any limitation as to the scope of use or functionality of any aspect of the invention.

Embodiments of the invention may be described in the general context of computer-executable instructions, such as program modules, executed by one or more computers or other devices. The computer-executable instructions may be organized into one or more computer-executable components or modules. Generally, program modules include, but are not limited to, routines, programs, objects, components, and data structures that perform particular tasks or implement particular abstract data types. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

What is claimed is:

1. A system for detecting an object, said system comprising:
    a photodetector configured to receive light from a whispering gallery mode (WGM) resonator; and
    a processor coupled to the photodetector and programmed to:
        create a transmission spectrum based on the received light;
        identify an input mode within the transmission spectrum; and
        determine a presence of an object proximate to the WGM resonator based on detecting a splitting of the input mode into a first split mode and a second split mode.

2. The system of claim 1, wherein the processor is further programmed to determine the presence of a subsequent object proximate to the WGM resonator based on a change in the distance between the first split mode and the second split mode.

3. The system of claim 1, wherein the processor is further programmed to determine a presence of a subsequent object proximate the WGM resonator based on a change in a linewidth of at least one of the first split mode and the second split mode.

4. The system of claim 1, wherein the photodetector is a first photodetector configured to receive light from a first WGM resonator, and the object is a first object, said device comprising a second photodetector coupled to the processor and configured to receive light from a second WGM resonator, wherein the processor is further configured to determine a presence of a second object based on the light received by the second photodetector.

5. The system of claim 1, wherein the processor is further programmed to determine, based on the first split mode and the second split mode, one or more of the following: a polarizability of the object, a size of the object, and a refractive index of the object.

6. The system of claim 1, further comprising a communication interface coupled to the processor and configured to transmit a detection signal indicating the presence of the object.

7. A system for detecting an object, said system comprising:
    a photodetector configured to:
        receive light emitted by an active whispering gallery mode (WGM) microcavity laser, wherein the received light includes a first laser mode and a second laser mode, each of the first mode and the second mode representing light transmission in a frequency range; and
        combine the first laser mode and the second laser mode to create a heterodyne beat signal; and
    a processor coupled to the photodetector and programmed to:
        determine a first beat frequency based on the heterodyne beat signal at a first time;
        determine a second beat frequency based on the heterodyne beat signal at a second time; and
        determine a presence of an object proximate to the WGM microcavity laser based on a comparison of the first beat frequency and the second beat frequency.

8. The system of claim 7, wherein the light coupled out of the WGM microcavity laser further includes residual light from a light source, the system further comprising a wavelength-division multiplexer coupled to the photodetector and configured to:
    receive the light coupled out of by the WGM microcavity laser; and
    separate the residual light from the received light to create filtered light, wherein the photodetector receives the filtered light from the wavelength-division multiplexer.

9. The system of claim 7, wherein the processor is programmed to determine at least one of the first beat frequency and the second beat frequency at least in part by applying a fast Fourier transform to the heterodyne beat signal.

10. The system of claim 7, further comprising:
    the WGM microcavity laser;
    a light source; and
    a waveguide extending from the light source to the photodetector and proximate to the WGM microcavity laser, wherein the waveguide is configured to:
        transmit light from the light source to the WGM microcavity laser; and
        transmit the light emitted by the WGM microcavity laser to the photodetector.

11. The system of claim 10, wherein the WGM microcavity laser comprises a surface including an object adhesive, wherein the object adhesive is selected to bind the object to the surface.

12. The system of claim 10, wherein the light source comprises a substantially monochromatic laser.

13. A method comprising:
    receiving, by a photodetector, light emitted by an active whispering gallery mode (WGM) microcavity laser;
    creating, by the photodetector a heterodyne beat signal based on the received light;
    determining, by a processor, a first beat frequency based on the heterodyne beat signal at a first time;
    determining by a processor a second beat frequency based on the heterodyne beat signal at a second time; and
    determining, by the processor, a presence of an object proximate to the WGM microcavity laser based on a comparison of the first beat frequency and the second beat frequency.

14. The method of claim 13, wherein the received light includes a plurality of input laser modes representing light transmission in a plurality of frequency ranges.

15. The method of claim 14, wherein at least one of the plurality of inout laser modes is split into a plurality of split laser modes, and creating the heterodyne beat signal further comprises combining the plurality of split laser modes.

16. The system of claim 1, wherein the WGM resonator comprises a WGM resonator doped with a gain medium.

17. A method comprising:
- receiving, by a photodetector, light from a whispering gallery mode (WGM) resonator;
- creating a transmission spectrum based on the received light;
- identifying an input mode within the transmission spectrum; and
- determining a presence of an object proximate to the WGM resonator based on a splitting of the input mode into a first split mode and a second split mode.

18. The method of claim 17 further comprising determining, based on the first split mode and the second split mode, a polarizability of the object.

19. The method of claim 17, further comprising detecting the presence of a subsequent object based on at least one of a distance between the first split mode and the second split mode and a linewidth of at least one of the first split mode and the second split mode.

20. The method of claim 17 further comprising receiving a plurality of input modes representing light transmission in a plurality of frequency ranges, wherein at least one of the input modes is split into a plurality of split modes.

* * * * *